US011562822B2

United States Patent
Morishima et al.

(10) Patent No.: US 11,562,822 B2
(45) Date of Patent: Jan. 24, 2023

(54) INFORMATION PROCESSING METHOD, INFORMATION PROCESSING DEVICE, AND INFORMATION PROCESSING SYSTEM

(71) Applicant: HOYA CORPORATION, Tokyo (JP)

(72) Inventors: Takayoshi Morishima, Tokyo (JP); Keiji Ito, Tokyo (JP); Kohei Iketani, Tokyo (JP); Atsushi Watabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 82 days.

(21) Appl. No.: 17/253,344

(22) PCT Filed: Nov. 21, 2019

(86) PCT No.: PCT/JP2019/045607
§ 371 (c)(1),
(2) Date: Dec. 17, 2020

(87) PCT Pub. No.: WO2020/110898
PCT Pub. Date: Jun. 4, 2020

(65) Prior Publication Data
US 2021/0265052 A1     Aug. 26, 2021

(30) Foreign Application Priority Data
Nov. 30, 2018   (JP) ............................. JP2018-225895

(51) Int. Cl.
*G16H 40/40*     (2018.01)
*A61B 1/00*     (2006.01)
*A61B 1/05*     (2006.01)
*A61B 1/06*     (2006.01)
*A61B 1/12*     (2006.01)

(52) U.S. Cl.
CPC ........... *G16H 40/40* (2018.01); *A61B 1/0011* (2013.01); *A61B 1/00016* (2013.01);
(Continued)

(58) Field of Classification Search
CPC ... A61B 1/00103; A61B 1/05; A61B 1/00016; A61B 1/00059; A61B 1/00105;
(Continued)

(56) References Cited

U.S. PATENT DOCUMENTS

| 8,972,714 B2 | 3/2015 | Talbert et al. |
| 9,295,377 B2 | 3/2016 | Oneda et al. |

(Continued)

FOREIGN PATENT DOCUMENTS

| JP | 2002-166261 | 6/2002 |
| JP | 2005-122707 | 5/2005 |

(Continued)

OTHER PUBLICATIONS

Official Communication issued in International Bureau of WIPO Patent Application No. PCT/JP2019/045607, dated Jan. 21, 2020.

*Primary Examiner* — Michael J Carey
*Assistant Examiner* — Christen A. Sharpless
(74) *Attorney, Agent, or Firm* — Greenblum & Bernstein, P.L.C.

(57) ABSTRACT

A device, system, and method that: acquires information that a sterilized endoscope, having reusable and non-reusable parts, is used; outputs an instruction for collecting the used endoscope from a medical institution; acquires information on the number of endoscopes scheduled for inspection, a predetermined number of endoscopes not scheduled for inspection, and the number of endoscopes in an endoscope inventory; outputs an instruction for delivering a non-used replaceable endoscope to the institution in response to the collection instruction; and outputs an instruction for delivering a non-used endoscope to the institution when equation (2) is not satisfied, equation (2) being: endoscope inventory quantity>number of endoscopes scheduled for inspection+predetermined number.

9 Claims, 20 Drawing Sheets

(52) U.S. Cl.
CPC ...... *A61B 1/00059* (2013.01); *A61B 1/00103*
(2013.01); *A61B 1/00105* (2013.01); ***A61B
1/05* (2013.01); *A61B 1/06* (2013.01); *A61B
1/121*** (2013.01)

(58) Field of Classification Search
CPC ......... A61B 1/0011; A61B 1/06; A61B 1/121;
A61B 1/00057; G16H 40/40; G16H
40/20; G16H 70/20
USPC ........................................................ 600/109
See application file for complete search history.

(56) References Cited

U.S. PATENT DOCUMENTS

| | | |
|---|---|---|
| 10,413,165 B2 | 9/2019 | Talbert et al. |
| 2005/0103354 A1 | 5/2005 | Miyauchi et al. |
| 2007/0083286 A1* | 4/2007 | Kobayashi ............. G16H 40/20 700/214 |
| 2010/0298640 A1* | 11/2010 | Oneda ................ A61B 1/00105 600/109 |
| 2013/0131452 A1 | 5/2013 | Kuroda et al. |
| 2019/0261838 A1 | 8/2019 | Talbert et al. |

FOREIGN PATENT DOCUMENTS

| | | |
|---|---|---|
| JP | 2005-275618 | 10/2005 |
| JP | 2006-296675 | 11/2006 |
| JP | 2006-318038 | 11/2006 |
| JP | 2006296675 A * | 11/2006 |
| JP | 2010-092145 | 4/2010 |
| JP | 2012-164285 | 8/2012 |
| JP | 2013-524873 | 6/2013 |
| JP | 2018-041234 | 3/2018 |
| WO | 2009/081489 | 7/2009 |
| WO | 2012/032837 | 3/2012 |

* cited by examiner

FIG. 6

| ENDOSCOPE ID | REUSABLE PART ID | | | MODEL NAME | SCHEDULE | | | | |
|---|---|---|---|---|---|---|---|---|---|
| | DISTAL TIP ID | SCOPE CONNECTOR ID | LIGHT GUIDE ID | | ASSEMBLY COMPLETION DATE | STERILIZATION DAY | SHIPPING DATE | DATE OF COLLECTION | |
| S100 | A020 | B011 | C051 C052 | E001 | 2018/10/5 | 2018/10/22 | 2018/10/25 | 2018/11/25 | |
| S101 | A022 | B001 | C066 C067 | E001 | 2018/10/5 | 2018/10/22 | 2018/10/25 | | |

61

| USAGE STATUS | |
|---|---|
| MEDICAL INSTITUTION NAME | DATE OF USE |
| A CLINIC | 2018/11/25 |
| A CLINIC | |

| ENDOSCOPE ID | DEVICE NAME | LOCATION | DATE | | |
|---|---|---|---|---|---|
| | | | ARRIVAL DATE | DATE OF USE | DATE OF COLLECTION |
| S200 | E001 | – | 2018/10/25 | 2018/10/30 | 2018/10/30 |
| S201 | E001 | COLLECTION CONTAINER | 2018/10/25 | 2018/10/31 | |
| S222 | E001 | EXAMINATION ROOM | 2018/10/25 | | |
| S222 | E005 | EQUIPMENT ROOM | 2018/10/26 | | |

| REUSABLE PART ID | STATE |
|---|---|
| A001 | REMANUFACTURING |

| FREQUENCY | ENDOSCOPE ID | DATE | | | PART INSPECTION | |
|---|---|---|---|---|---|---|
| | | REMANUFACTURING INPUT DATE | SHIPPING DATE | COLLECTION DATE | INSPECTION DATE | RESULT |
| FIRST TIME | S200 | 2018/8/27 | 2018/9/5 | 2018/9/25 | 2018/10/1 | OK |
| SECOND TIME | S305 | 2018/10/5 | 2018/10/15 | 2018/10/29 | 2018/10/31 | OK |
| THIRD TIME | S380 | 2018/11/1 | | | | |

| MEDICAL INSTITUTION NAME | ENDOSCOPE ID | COLLECTION SITUATION | |
|---|---|---|---|
| | | ARRANGEMENT | COMPLETION |
| D INTERNAL MEDICINE HOSPITAL | S515 | YES | YES |
| H CIVIC HOSPITAL | S408 | YES | NO |
| CLINIC A | S500 | NO | NO |

| ENDOSCOPE ID | DEPARTURE LOCATION | DESTINATION | DEPARTURE DATE AND TIME | ARRIVAL DATE AND TIME |
|---|---|---|---|---|
| S511 | FIRST WAREHOUSE | B UNIVERSITY HOSPITAL | 2018/10/20 9:00 | 2018/10/20 10:00 |
| S487 | B UNIVERSITY HOSPITAL | FIRST FACTORY | 2018/10/20 10:10 | |
| S513 | FIRST WAREHOUSE | C CLINIC | | |

| INSPECTION SCHEDULE DATE | MODEL NAME |
|---|---|
| 2018/10/30 | E001 |
| 2018/10/30 | E100 |
| 2018/11/1 | E001 |

FIG. 15

| MEDICAL INSTITUTION NAME | MARGIN | | |
|---|---|---|---|
| | E001 | E002 | E003 |
| A CLINIC | 3 | 3 | 2 |
| B INTERNAL MEDICINE | 10 | 5 | 10 |
| C UNIVERSITYHOSPITAL | 25 | 20 | 20 |

… (1) …

INFORMATION PROCESSING METHOD, INFORMATION PROCESSING DEVICE, AND INFORMATION PROCESSING SYSTEM

TECHNICAL FIELD

The present invention relates to an information processing method, an information processing device, and an information processing system.

BACKGROUND ART

After the endoscopic examination is performed, reprocessing such as cleaning, disinfection, and sterilization of the used endoscope is required. Since the endoscope has a plurality of narrow pipelines such as channels, the reprocessing requires labor and time.

An endoscope separated into a video capsule and an endoscope body has been proposed (Patent Literature 1). A video capsule is a unit that encapsulates an image sensor, an imaging lens, and a light emitting element which are expensive parts among parts that constitute an endoscope. The video capsule do not have narrow pipelines such as channels, and therefore, can be easily reprocessed. The endoscope body is a so-called single-use that is discarded after being used once. The video capsule is reprocessed in a medical institution and attached to a distal tip of a new endoscope body to perform the endoscopic examination.

CITATION LIST

Patent Literature

Patent Literature 1: US 2010/0298640 A

SUMMARY OF INVENTION

Technical Problem

However, the endoscope disclosed in Patent Literature 1 is used by being assembled to the endoscope body after the video capsule is reprocessed by medical workers such as a doctor or a nurse. It is difficult to realize a structure that can be easily and reliably assembled by busy medical workers in areas where miniaturization is important, such as the distal tip of the endoscope insertion portion. Therefore, a new burden may be placed on a health-care personnel One aspect is to provide an information processing method or the like that reduces a burden on a health-care personnel engaging in endoscopic examination.

Solution to Problem

An information processing method includes acquiring use information indicating that a sterilized endoscope in which a reusable part that is able to be used repeatedly and a non-reusable part that is able to be used only once are combined is used, outputting a collection instruction for collecting the endoscope corresponding to the acquired use information from a medical institution, and outputting a delivery instruction for delivering a non-used replaceable endoscope to the medical institution.

Advantageous Effects of Invention

According to one aspect, it is possible to provide the information processing method or the like that reduces the burden on the health-care personnel engaging in the endoscopic examination.

BRIEF DESCRIPTION OF DRAWINGS

FIG. 6 is an explanatory diagram for explaining a record layout of a first endoscope DB.
FIG. 7 is an explanatory diagram for explaining a record layout of a second endoscope DB.
FIG. 8 is an explanatory diagram for explaining a record layout of a reusable part DB.
FIG. 9 is an explanatory diagram for explaining a record layout of a collection request DB.
FIG. 10 is an explanatory diagram for explaining a record layout of a slip DB.
FIG. 15 is an explanatory diagram for explaining a record layout of a margin DB.

DESCRIPTION OF EMBODIMENTS

First Embodiment

Figure 1:
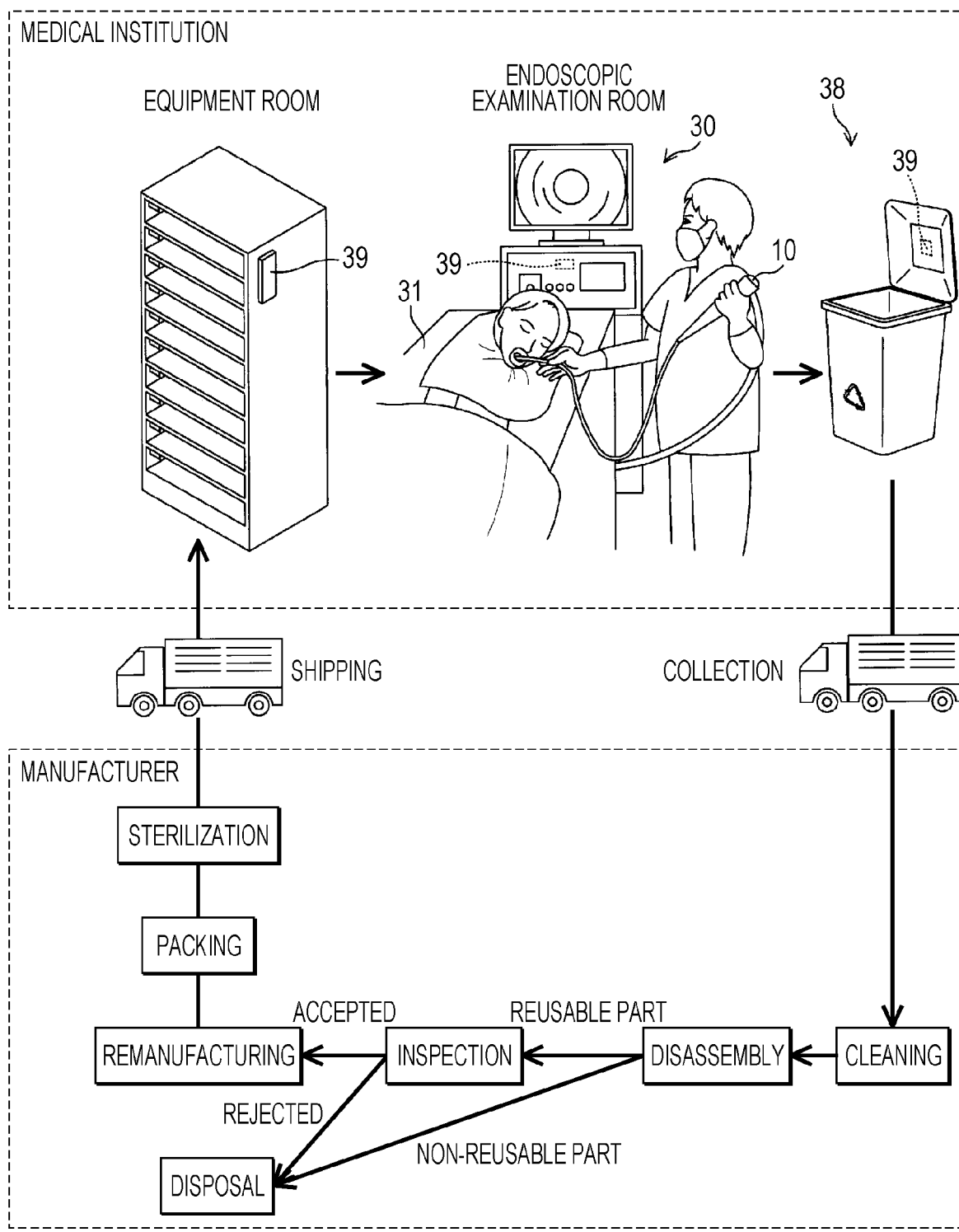
FIG. 1 is an explanatory diagram for explaining an outline of a system that provides an endoscope.

FIG. 1 is an explanatory diagram for explaining an outline of a system that provides an endoscope 10. A manufacturer who remanufactures the endoscope 10 delivers the packed and sterilized endoscope 10 to an equipment room of a medical institution. The equipment room is provided with a rack in which various models of endoscopes 10 are organized and housed. A delivery worker houses the endoscope 10 on the rack.

In the medical institution, the endoscope 10 is taken out from the equipment room and transported to the endoscopic examination room as needed. In the endoscopic examination room, the endoscope 10 is taken out from the sterilization pack and used for the endoscopic examination. The used endoscope 10 is put into a collection container 38.

An endoscope tag 18 (see FIG. 3) is attached to the endoscope 10. An endoscope identifier (ID) uniquely assigned to the endoscope 10 is recorded in the endoscope tag 18. A tag reader 39 is attached to a part or all of the equipment room, the endoscopic examination room, and the collection container 38. The tag reader 39 may be attached to various places where the endoscope 10 can move, such as a corridor between the equipment room and the endoscope room.

The tag reader 39 reads the endoscope tag 18, so it is detected that the endoscope 10 is taken out from the equipment room and used for endoscopic examination. Based on the detection result, the manufacturer is notified of the use information indicating that the endoscope 10 has been used. A manufacturer is a re-manufacturer that performs remanufacturing of a single-use device (SUD). The manufacturer may also serve as a medical device manufacturer that manufactures new medical devices. The manufacturer collects the used endoscope 10 from the collection container 38 and delivers the replaceable endoscope 10 to the equipment room.

Since a new endoscope 10 is delivered to the equipment room each time the endoscope 10 is used, there is no need to manage the inventory of the endoscope 10 in the medical institution. Since the delivered endoscope 10 is sterilized, pre-case sterilization is not required. Since the used endoscope 10 is collected by the manufacturer, reprocessing and maintenance between cases are not required. As a result, the burden on the health-care personnel engaging in the endoscopic examination is reduced. Therefore, the medical worker can focus on medical practices such as the endoscopic examination and a patient care.

The endoscope 10 collected from the collection container 38 is shipped to a remanufacturing factory. In the remanufacturing factory, the endoscope 10 is subjected to cleaning, disinfection and sterilization treatments. Thereafter, the endoscope 10 is disassembled by a predetermined procedure and separated into a non-reusable part and a reusable part. The non-reusable part is discarded.

The non-reusable part is, for example, a thin tube whose inner surface is difficult to reprocess, a forceps plug 23 which is complicated in shape and difficult to reprocess, parts which cannot withstand multiple sterilization processes, and the like. Parts that are destroyed during disassembly and parts that are cheaper to use new parts than costs of performing quality inspection for reusing are also non-reusable parts.

All reusable parts can be made into reusable parts in terms of quality and cost. Among them, since a unit in which an image sensor 131 (see FIG. 5) and an imaging lens are combined is expensive and has high durability which can withstand multiple uses, the unit should preferably be a reusable part.

Each reusable part is subjected to a predetermined quality inspection. Parts that do not accept the quality inspection are discarded. Parts that accept the quality inspection are put into the remanufacturing process. In the remanufacturing process, the reusable part and the new non-reusable part are combined to assemble a new endoscope 10.

The assembled endoscope 10 is packed in a sterilization pack through a predetermined inspection process, and is sterilized by, for example, an electron beam sterilization, and the like. With the above, the new endoscope 10 is completed. The completed endoscope 10 is delivered to the medical institution in exchange for the used endoscope 10 as described above.

The manufacturer regularly charges the medical institution for the usage fee of the endoscope 10 based on the contract with the medical institution. The usage fee is calculated based on, for example, Equation (1).

$$\text{Monthly charge} = \text{Basic charge} + 1 \text{ charge} \times \text{Number of endoscopes replaced} \tag{1}$$

The fee may be determined based on the number of endoscopes 10 that have received the collection request. The fee may be determined based on any calculation method based on the contract.

Figure 2:
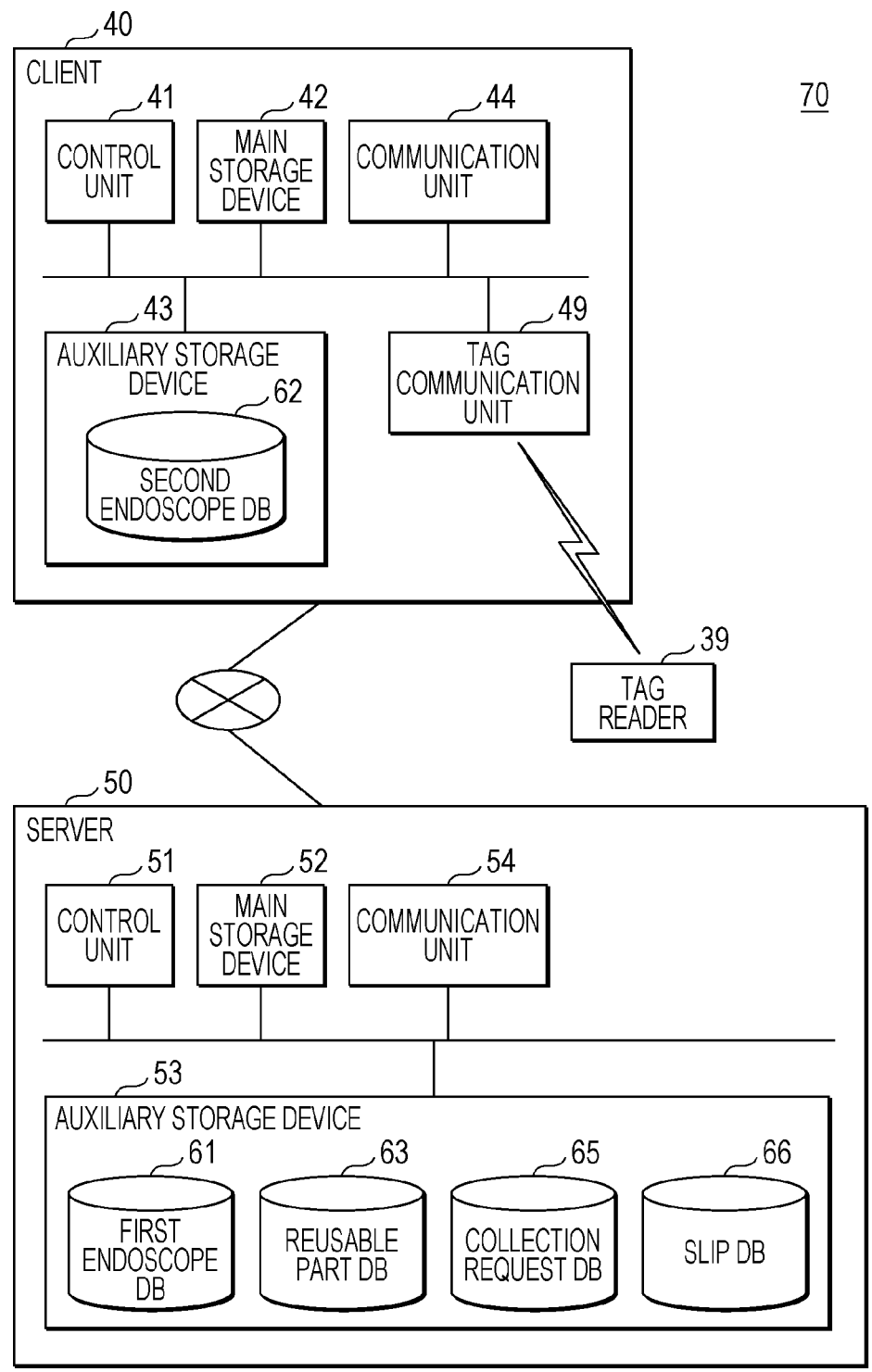
FIG. 2 is an explanatory diagram for explaining a configuration of an information processing system.

FIG. 2 is an explanatory diagram for explaining a configuration of an information processing system 70. The information processing system 70 includes a client 40 and a server 50 connected via a network such as the Internet. The client 40 is located in each medical institution.

The client 40 includes a control unit 41, a main storage device 42, an auxiliary storage device 43, a communication unit 44, a tag communication unit 49, and a bus. The control unit 41 is an arithmetic control device that executes the program of the first embodiment. One or more central processing units (CPUs), multi-core CPUs, and the like are used for the control unit 41. The control unit 41 is connected to each part of hardware constituting the client 40 via the bus.

The main storage device 42 is a storage device such as a static random access memory (SRAM), a dynamic random access memory (DRAM), and a flash memory. The main storage device 42 temporarily stores information required during the processing performed by the control unit 41 and a program being executed by the control unit 41.

The auxiliary storage device 43 is a storage device such as the SRAM, the flash memory, or a hard disk. The auxiliary storage device 43 stores a second endoscope database (DB) 62, a program to be executed by the control unit 41, and various data necessary for executing the program. Note that the second endoscope DB 62 may be stored in an external large-capacity storage device or the like connected to the client 40. The second endoscope DB 62 may be recorded in an electronic medical chart system.

The communication unit 44 is an interface for communication between the client 40 and the network. The tag communication unit 49 communicates with the tag reader 39 arranged in the equipment room or the like by wireless or wired communication.

As described above, the tag reader 39 reads the endoscope ID recorded on the endoscope tag 18. The tag reader 39 is a reading device using short-range wireless communication such as a radio frequency identifier (RFID) reading device or an ID tag reading device. The endoscope tag 18 is a short-range wireless communication tag such as an RFID tag or an ID tag.

The endoscope tag 18 and the tag reader 39 may communicate with each other via any wireless communication method such as Bluetooth (registered trademark), a wireless local area network (LAN), or near field communication (NFC).

The tag reader 39 may be an optical reading device such as a QR code (registered trademark) reader or a barcode reader, and the endoscope tag 18 may be an optical tag such as a QR code or a barcode. The tag reader 39 may be a barcode reader, a smartphone, a tablet, or a digital camera. The tag reader 39 notifies a client 40 when the movement of the endoscope 10 is detected.

The client 40 of the first embodiment is a general-purpose personal computer, a tablet, or the like. The client 40 may be connected to a network via an in-hospital network system (not illustrated). The client 40 may be integrated with an in-hospital system such as an electronic medical record system or a medical appointment system.

The server 50 includes a control unit 51, a main storage device 52, an auxiliary storage device 53, a communication unit 54, and a bus. The control unit 51 is an arithmetic control device that executes the program of the first embodiment. One or more CPUs, multi-core CPUs, and the like are used for the control unit 51. The control unit 51 is connected to each part of hardware constituting the server 50 via the bus.

The main storage device 52 is a storage device such as SRAM, DRAM, and/or flash memory. The main storage device 52 temporarily stores information required during the processing performed by the control unit 51 and a program being executed by the control unit 51.

The auxiliary storage device 53 is a storage device such as the SRAM, the flash memory, the hard disk, or a magnetic disk. The auxiliary storage device 53 stores a first endoscope DB 61, a reusable part DB 63, a collection request DB 65, a slip DB 66, a program to be executed by the control unit 51, and various data necessary for executing the program. Note that the first endoscope DB 61, the reusable part DB 63, the collection request DB 65, and the slip DB 66 may be stored in an external large-capacity storage device and the like connected to the server 50.

The communication unit 44 is an interface for communication between the server 50 and the network. The server 50 of the first embodiment is a general-purpose personal computer, a large-scale computer, or a virtual machine running on the large-scale computer. The server 50 may be realized by distributed processing using a plurality of computers.

Figure 3:
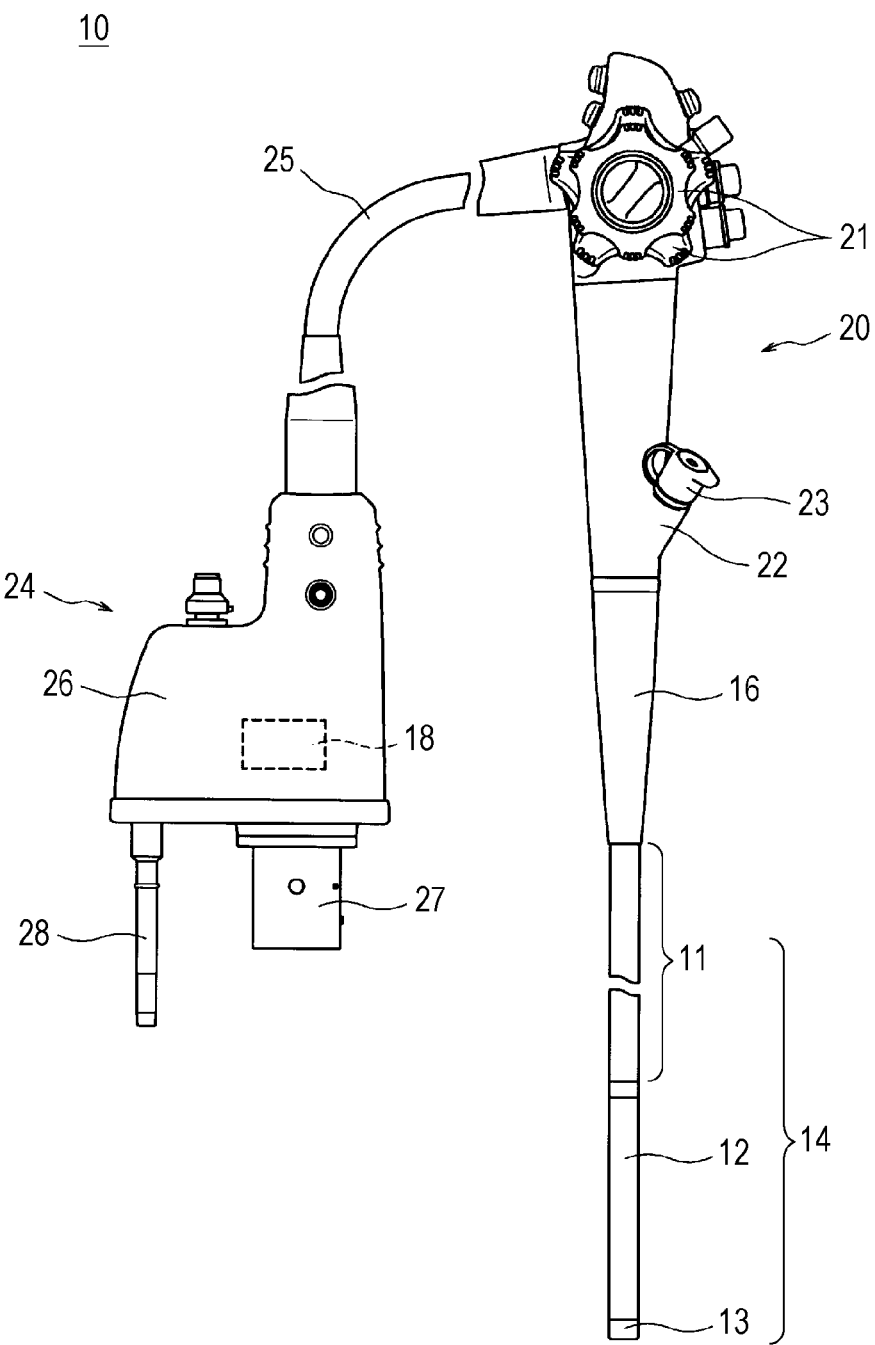
FIG. 3 is an external view of the endoscope.

FIG. 3 illustrates an external view of the endoscope 10. The endoscope 10 of the first embodiment is a flexible mirror for a gastrointestinal tract. The endoscope 10 has an insertion portion 14, an operation unit 20, a universal code 25 and a connector unit 24. The operation unit 20 has a bending knob 21 and a channel entrance 22. The forceps plug 23 having an insertion port for inserting a treatment tool or the like is fixed to the channel entrance 22.

The insertion portion 14 is long and one end thereof is connected to the operation unit 20 via a stopper 16. The insertion portion 14 has a soft portion 11, a bending section 12, and a distal tip portion 13 in this order from the operation unit 20 side. The bending section 12 is bent in response to the operation of the bending knob 21.

In the following description, a longitudinal direction of the insertion portion 14 will be referred to as an insertion direction. Similarly, the side closer to the operation unit 20 along the insertion direction is described as the operation unit side, and the side far from the operation unit 20 is described as the distal tip side.

The universal code 25 is long, and a first end thereof is connected to the operation unit 20 and a second end thereof is connected to the connector unit 24. The connector unit 24 is covered with a substantially rectangular parallelepiped connector case 26. The scope connector 27 and the light guide connector 28 protrude from one side of the connector case 26. The endoscope tag 18 is attached to the surface or inside of the connector case 26. The connector unit 24 is connected to a processor 32 for endoscope (see FIG. 4), an air supply/water supply device, and the like.

Figure 4:
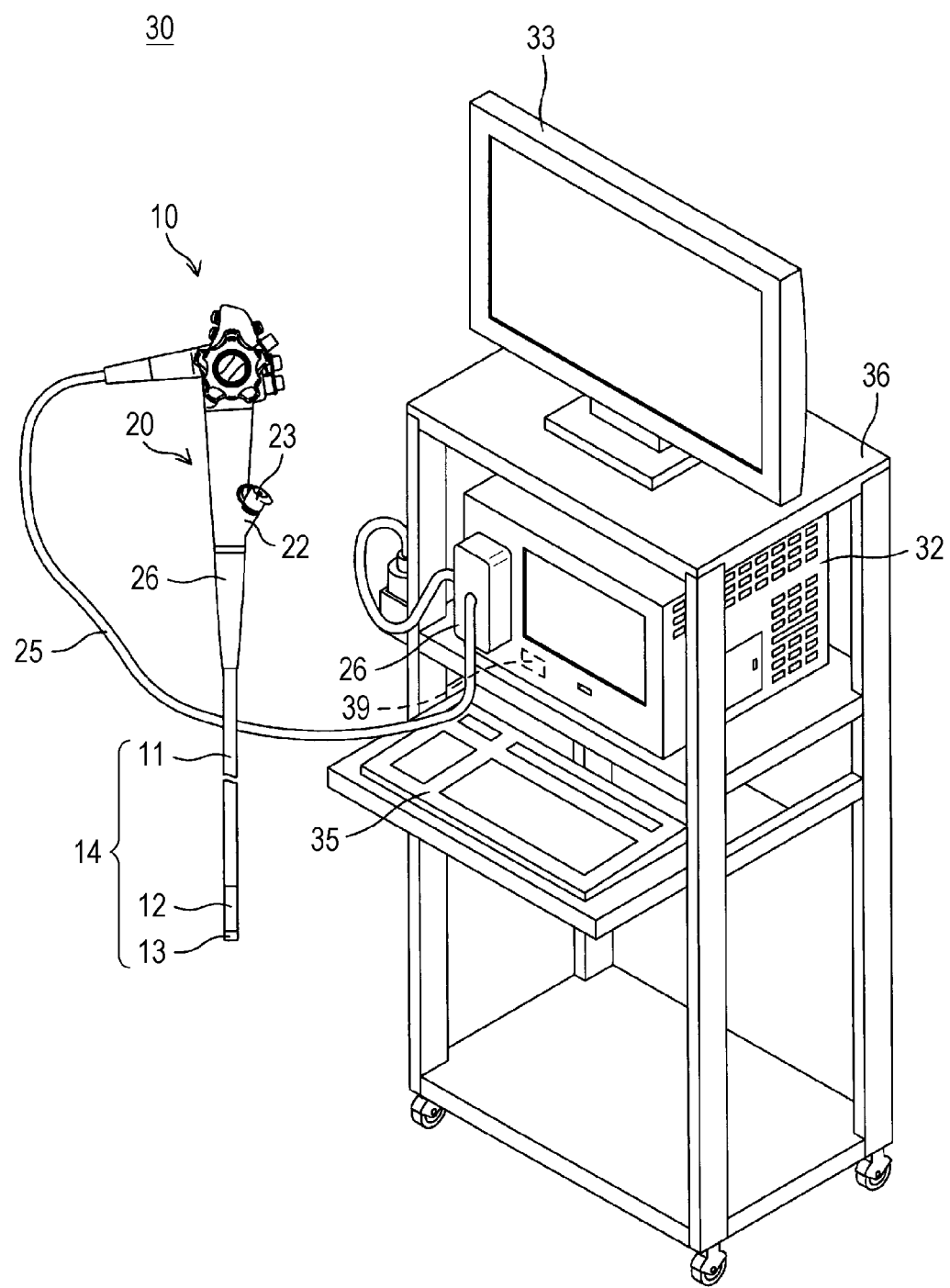
FIG. 4 is an external view of the endoscope system.

FIG. 4 illustrates an external view of the endoscope system 30. The endoscope system 30 includes the processor 32 for endoscope, the endoscope 10, and a display device 33. The display device 33 is, for example, a liquid crystal display device or an organic electro luminescence (EL) display device.

The display device 33 is installed on an upper stage of a housing rack 36 with a caster. The processor 32 for endoscope is housed in a middle stage of the housing rack 36. The housing rack 36 is disposed near a bed 31 for endoscopic examination (see FIG. 1). The housing rack 36 has a pull-out rack with a keyboard 35 connected to a processor 32 for endoscope.

The outline of the endoscopic examination will be described. The housing rack 36 is disposed near the bed 31 for endoscopic examination. The endoscope 10 of the model corresponding to the inspection is taken out from the equipment room and transported to the endoscopic examination room. The endoscope tag 18 and the tag reader 39 detect locations of each endoscope 10 and record the detected locations in the second endoscope DB 62.

The endoscope 10 taken out from the sterilization pack is connected to the processor 32 for endoscope, and thus the predetermined operation check is performed. The endoscopic examination of the patient lying in the bed 31 for endoscopic examination is performed. During the endoscopic examination, an image captured by the endoscope 10 is displayed on the display device 33 in real time.

After the endoscopic examination is completed, the endoscope 10 is removed from the processor 32 for endoscope. The endoscope 10 is packed one by one in, for example, the original sterilization pack, a plastic bag, or the like. The packed endoscope 10 is put into the collection container 38.

Figure 5:
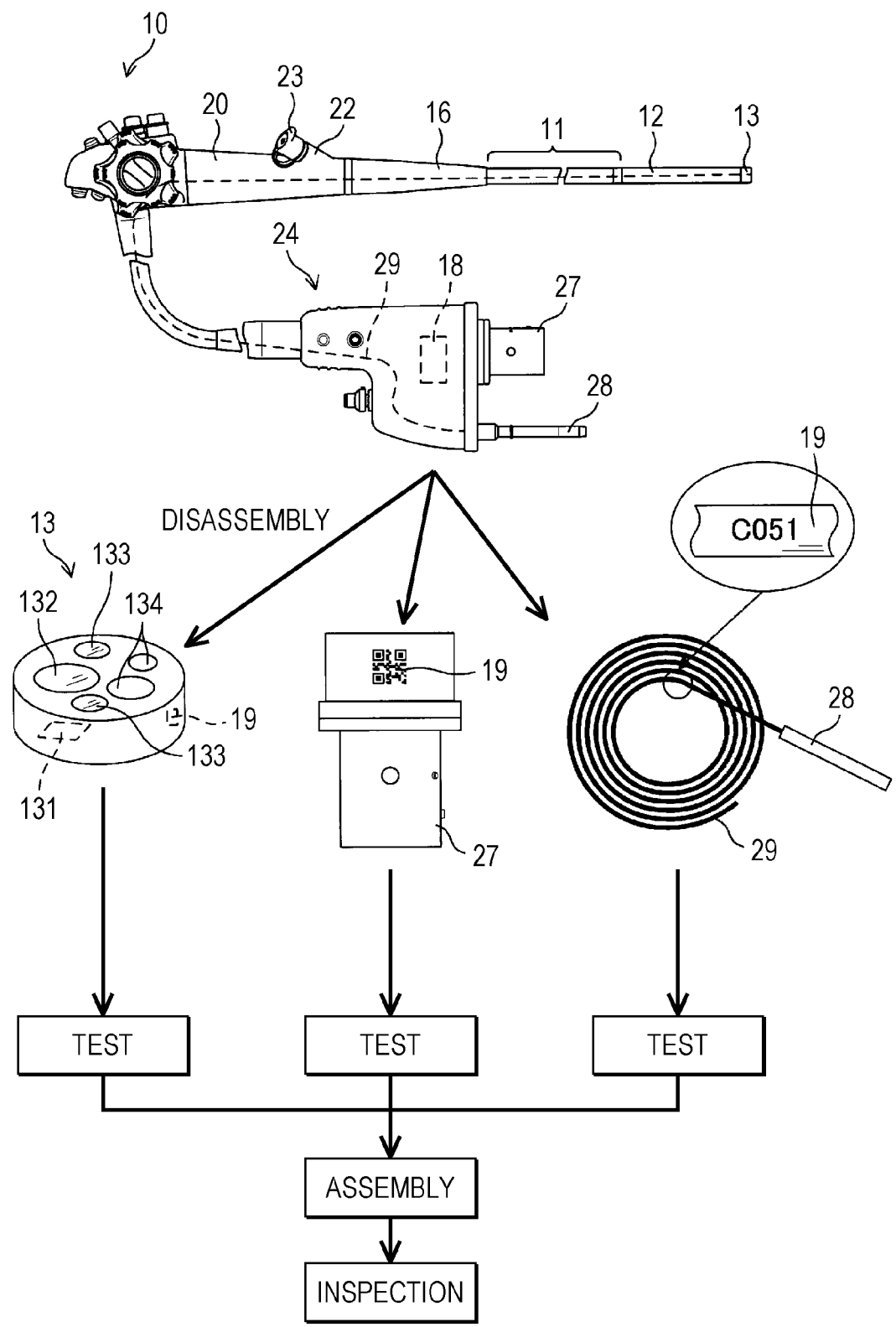
FIG. 5 is an explanatory diagram for explaining a remanufacturing process of the endoscope.

FIG. 5 is an explanatory diagram for explaining the remanufacturing process of the endoscope 10. In the first embodiment, the case where the distal tip portion 13, the scope connector 27, and the light guide 29 are reusable parts will be described as an example. As described above, all reusable parts in terms of quality and cost can be reused parts. Only one of the parts that can be made into the reusable part may actually be made into a reusable part.

The endoscope 10 collected from the collection container 38 is shipped to a remanufacturing factory. At the remanufacturing factory, the endoscope 10 is taken out from a packing material such as the sterilization pack or the plastic bag. The endoscope 10 is subjected to the cleaning, disinfection, and sterilization processes. As a result, the endoscope 10 is ready for safe handling in the remanufacturing process.

It is preferable to incinerate the endoscope 10 that can be contaminated with pathogens that cannot be removed by normal treatment, such as abnormal prion, without removing the endoscope 10 from the packaging material. By packing the used endoscopes 10 one by one and then putting the endoscopes into the collection container 38, even when the endoscope 10 that can be contaminated by the abnormal prion and the like occurs, only the corresponding endoscope 10 is incinerated, and other endoscopes 10 can be put into the remanufacturing process.

For example, it is desirable to incinerate the endoscope 10 that cannot be processed in general procedures such as the endoscope 10 where perforation occurs due to the treatment device used together, without taking out the endoscope from the packing material. It is possible to prevent a disassembly worker or the like from getting infected.

Note that before cleaning, a living tissue remaining in the endoscope 10 may be collected and examined. For example, when the abnormal prion, infectious microorganisms that are not detected from normal patients, or the like is detected, it is desirable to prevent a disassembly worker or the like from getting infected by incinerating the endoscope 10. Furthermore, it is possible to contribute to the prevention of nosocomial infections and the like by notifying the medical institution using the endoscope 10 of the endoscope ID and the inspection result.

The endoscope 10 is disassembled according to a predetermined procedure. The non-reusable part is discarded. The reusable part in the first embodiment will be described.

The distal tip portion 13 is a disk shape provided with a through hole 134 penetrating in a thickness direction, and has an observation window 132 and two illumination windows 133 on one surface. The observation window 132 and the illumination window 133 are covered with a transparent plate such as plastic or glass. An image sensor 131 and a lens on which an optical image on the surface of the image sensor 131 is formed are arranged inside the observation window 132. The distal tip portion 13 has a terminal or a connector used to connect a signal line and a power line to the image sensor 131.

The distal tip portion 13 is provided with a through hole 134 that penetrates in the thickness direction. Furthermore, a part tag 19 in which a part ID uniquely assigned to each reusable part is recorded is embedded in the distal tip portion 13. The part tag 19 is constituted by a small wireless chip for a short-range wireless communication tag such as an RFID tag or an ID tag. The part tag 19 may be a two-dimensional barcode.

The scope connector 27 is a substantially stepped cylindrical type, and has a connector pin (not illustrated) provided therein. The part tag 19 on which the part ID is recorded is attached to or printed on the scope connector 27. The part tag 19 is, for example, a two-dimensional barcode. The part tag 19 may be constituted by a small wireless chip for a short-range wireless communication tag such as an RFID tag or an ID tag.

The light guide 29 is an optical fiber bundle covered with a protective tube. A light guide connector 28 is attached to one end of the light guide 29. An illumination lens (not illustrated) is attached to the other end of the light guide 29. In the assembled endoscope 10, the illumination lens is arranged inside the illumination window 133.

The protective tube is provided with the part tag 19 on which the part ID is printed, for example, by laser marking. Note that the part ID may be encrypted and recorded in the part tag 19. The part tag 19 may be marked with a barcode indicating the part ID. The part tag 19 may be constituted by a small wireless chip for a short-range wireless communication tag such as an RFID tag or an ID tag.

The reusable part for which it is difficult to provide the part tag 19 may be housed, for example, in a case provided with an identification tag after being removed from the endoscope 10. Since the endoscope ID is associated with each component ID by the first endoscope DB 61, the tag provided on the case can be associated with the component ID.

A predetermined quality test is performed on each reusable part taken out from the endoscope 10. The reusable parts that do not accept the quality test are discarded. Note that the reusable part that is used a predetermined number of times may be discarded without performing the quality test. The use frequency of each reusable part is used is recorded in the reusable part DB 63 described later.

When a chip or the like capable of rewriting or adding an RFID tag or the like is used for the part tag 19, the use frequency may be recorded in the reusable part that accepts the quality test. The use frequency or the like may be marked on the reusable part by laser marking or the like. It is possible to check the use frequency of each reusable part without accessing the reusable part DB 63.

The reusable part that accepts the quality inspection and the new non-reusable part are combined to assemble a new endoscope 10. Note that when the number of reusable parts is insufficient, a new reusable part is used. A predetermined quality inspection is performed on the assembled endoscope 10.

Note that the result of the quality test may be written in the part tag 19. For example, when the acceptance criteria for the reusable part differ depending on the model of the endoscope 10, a new endoscope can be assembled using the appropriate combination of parts by writing the result of the quality test in the part tag.

The reusable parts taken out from one endoscope 10 may be used for assembling the same endoscope 10. The endoscope 10 created by using the reusable part taken out from the endoscope 10 collected from one medical institution may be delivered to the same medical institution. The endoscope 10 may be assembled by randomly combining the reusable parts taken out from a plurality of endoscopes 10.

FIG. 6 is an explanatory diagram for explaining a record layout of the first endoscope DB 61. The first endoscope DB 61 is a DB that records the endoscope ID, the reusable part ID, the model name, the schedule, and the usage status in association with each other.

The first endoscope DB 61 has an endoscope ID field, a reusable part ID field, a model name field, a schedule field, and a usage status field. The reusable part ID field has a field related to the reusable part, such as a distal tip portion ID field, a scope connector ID field, and a light guide ID field.

The schedule field has an assembly completion date field, a sterilization date field, a shipping date field, and a collection date field. The usage status field has a medical institution name field and a date of use field.

The endoscope ID field records the endoscope ID. The distal tip portion ID field records the part ID of the distal tip portion 13. The scope connector ID field records the part ID of the scope connector 27. The light guide ID field records the part ID of the light guide 29.

The model name field records the model of the endoscope 10. The assembly completion date field records the date when the assembly is completed. The sterilization date field records the date when the sterilization is performed. The shipping date field date records the date when the endoscope 10 is shipped. The collection date field records the date when the endoscope 10 is collected from the medical institution.

The medical institution name field records the name of the medical institution that delivers the endoscope 10. The date of use field records the date when the endoscope 10 is used in the medical institution. The first endoscope DB 61 has one record for one endoscope 10.

FIG. 7 is an explanatory diagram for explaining a record layout of the second endoscope DB 62. The second endoscope DB 62 is a DB that records the endoscope ID, the model name, the location, and the date in association with each other. The second endoscope DB 62 has an endoscope ID field, a model name field, a location field and a date field. The date field has an arrival date field, a date of use field, and a collection date field.

The endoscope ID field records the endoscope ID. The model name field records the model of the endoscope 10. The location field records the location of the endoscope 10 acquired via the tag reader 39. "—" in the location field means that the endoscope 10 is collected by a manufacturer and does not exist in the medical institution.

The arrival date field records the date when the endoscope 10 was delivered from the manufacturer to the medical institution. The date of use field records the date when the endoscope 10 is used. The collection date field records the date when the endoscope 10 is collected by the manufacturer. A blank in the date of use field means that endoscope 10 has not been used yet. A blank in the collection date field means that the endoscope 10 has not yet been collected. The second endoscope DB 62 has one record for one endoscope 10.

FIG. 8 is an explanatory diagram for explaining a record layout of a reusable part DB 63. The reusable part DB 63 is a DB that records the reusable part ID, the state of the reusable part, and the state of the assembled endoscope 10 in association with each other. The state of the assembled endoscope 10 includes the endoscope ID, date, and the inspection status after collection and disassembly for each assembled endoscope. FIG. 8 illustrates one record for the reusable part DB 63. The reusable part DB 63 has one record for one reusable part.

The reusable part DB 63 has a reusable part ID field, a status field, a count field, an endoscope ID field, a date field, and a part inspection field. The date field has a remanufactured input date field, a shipping date field, and a collection date field. The part inspection field has an inspection date field and a result field.

The reusable part ID field records the part ID of the reusable part. The status field records the state of the reusable part. "Under remanufacturing" illustrated in FIG. 8 means that the endoscope 10 has not yet been completed after the reusable part was put into the remanufacturing process. The status field appropriately records, for example, "waiting for shipment" indicating that the endoscope 10 is completed and waiting for shipment, "waiting for collection" indicating that the endoscope 10 exists in the medical institution, "under disassembly" indicating that the endoscope 10 is collected and is being disassembled, and the like.

The count field records the usage count of the reusable part. The endoscope ID field records the endoscope ID of the endoscope 10 with which the reusable part is assembled. The reusable input date field records the date the reusable part is put into the remanufacturing process. The shipping date field records the date when the endoscope 10 is delivered to the medical institution. The collection date field records the date when the endoscope 10 is collected from the medical institution.

The inspection date field records the date when the reusable part taken out from the collected endoscope 10 is inspected. The result field records the test result. "OK" means that the inspection is accepted. When the inspection does not pass, "NG" is recorded in the result field and the reusable part is discarded.

FIG. 9 is an explanatory diagram for explaining a record layout of the collection request DB 65. The collection request DB 65 is a DB that records the medical institution name, the endoscope ID of the endoscope 10 that received the collection request, and the collection status in association with each other. The collection request DB 65 has a medical institution name field, an endoscope ID field, and a collection status field. The collection status field has an arrangement field and a completion field.

The medical institution name field records the name of the medical institution. The endoscope ID field records the endoscope ID. The arrangement field records an arrangement status of collection. "YES" indicates that the collection arrangement is completed, and "NO" indicates that the collection arrangement is not completed. The arrangement field records the completion status of collection. "YES" indicates that the collection is completed, and "NO" indicates that the collection arrangement is not completed.

The collection request DB 65 has one record for one endoscope 10 for which the use information is transmitted from the control unit 41 to the server 50 based on the fact that the tag reader 39 detects that the container was placed in the collection container 38.

FIG. 10 is an explanatory diagram for explaining a record layout of the slip DB 66. The slip DB 66 is a DB that records a delivery slip related to the delivery and collection of the endoscope 10. The slip DB 66 is shared, for example, with a logistics company or a logistics department of the manufacturer. The logistics company or logistics department will deliver and collect the endoscope 10 based on the slip DB 66.

The collection operation of the endoscope may be an operation of taking out the used endoscope 10 from collection container 38 and moving the used endoscope 10 to another container or may be an operation of moving the endoscope to each collection container 38 and installing a new collection container 38. In any case, the used endoscope 10 is so-called infectious waste, and the collection operation is carried out based on appropriate infection prevention measures.

The slip DB 66 has an endoscope ID field, a departure location field, a destination field, a departure date and time field, and an arrival date and time field. The endoscope ID field records the endoscope ID. The departure field location records the departure location. The destination field records the destination.

The departure date and time field records the date and time when the endoscope 10 is received and departed at the departure location. The arrival date and time field records the date and time when the endoscope 10 is delivered and departed at the departure location. The blanks in the departure date and time field and the arrival date and time field mean before departure or before arrival. The slip DB 66 has one record for one shipment of one endoscope 10.

When the logistics company receives the endoscope 10 based on the slip DB 66, the date and time is recorded in the receipt date and time field, and when the endoscope 10 is delivered, the date and time is recorded in the arrival date and time field. For example, the recording of the date and time to the arrival date and time field is performed by allowing, for example, a delivery worker to operate an information processing device such as a smartphone. The recording to the slip DB 66 may be automatically performed based on the signal from the tag reader 39 that is the equipment room of the medical institution, the transportation vehicle, the warehouse of the manufacturer, and the like.

Figure 11:
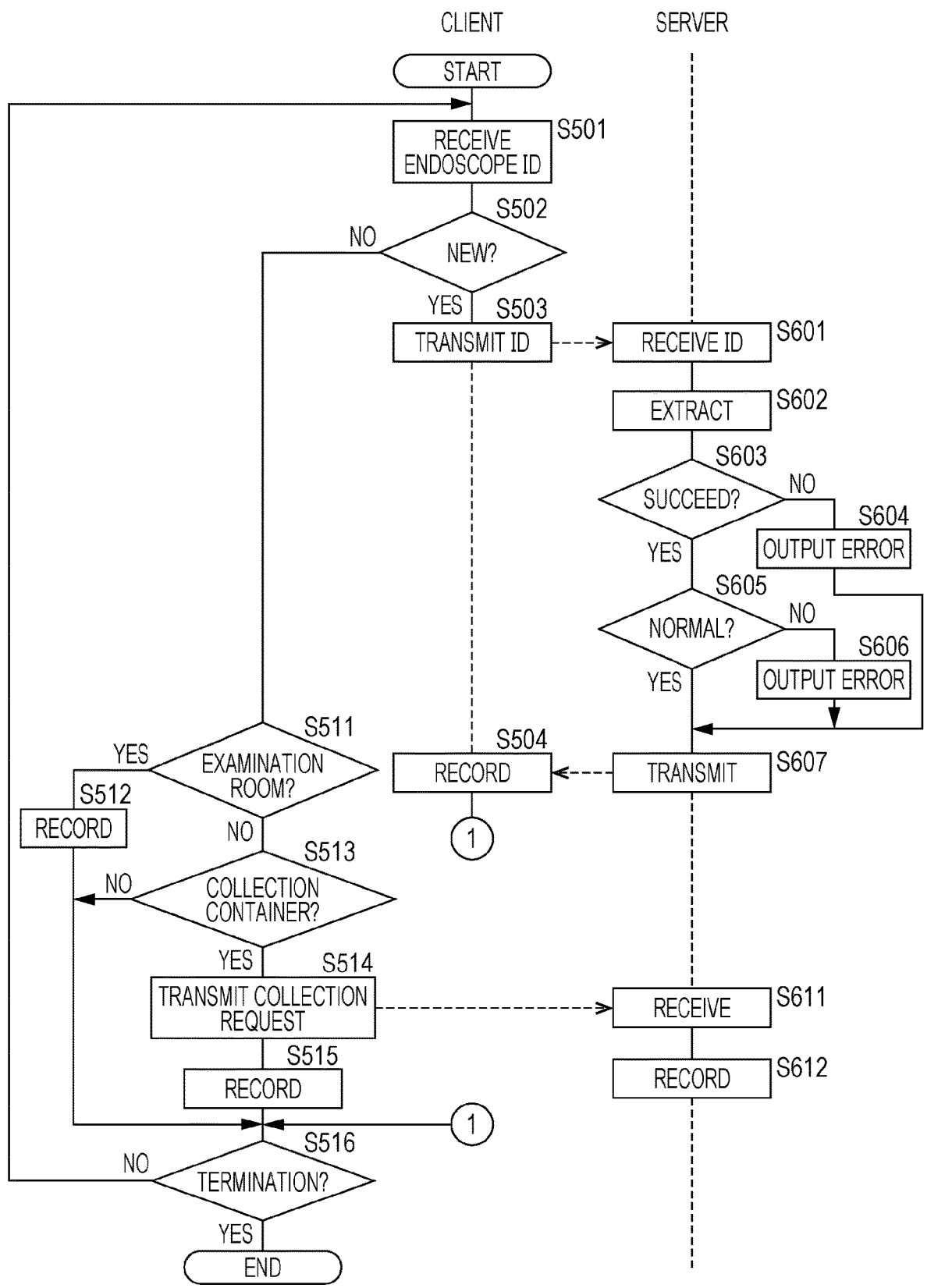
FIG. 11 is a flowchart for explaining a process flow of a program.

FIG. 11 is a flowchart for explaining a process flow of a program. As described above, the tag reader 39 transmits the endoscope ID and the detected location of the tag reader 39 to the client 40 when detecting the movement of the endoscope 10. The control unit 41 receives the endoscope ID and the installation location of the tag reader 39 from the tag reader 39 via the tag communication unit 49 (step S501).

The control unit 41 searches the second endoscope DB 62 using the endoscope ID as a key and extracts a record. The control unit 41 determines whether or not the record cannot be extracted, that is, whether or not the endoscope 10 is a newly detected endoscope 10 in the medical institution (step S502).

If it is determined that the endoscope 10 is newly detected (YES in step S502), the control unit 41 transmits the endoscope ID received in step S501 to the server 50 (step S503). Note that normally, the newly detected endoscope 10 is determined to be the newly delivered endoscope 10 to the equipment room.

The control unit 51 receives the endoscope ID (step S601). The control unit 51 searches the first endoscope DB 61 using the endoscope ID as a key and extracts a record (step S602). The control unit 51 determines whether or not the record extraction is successful (step S603).

For example, when the correct endoscope ID is not recorded on the endoscope tag 18, or when the tag reader 39 responds to a tag attached to an article other than the endoscope 10, the control unit 51 does not succeed in extracting the record. When it is determined that the record extraction does not succeed (NO in step S603), the control unit 51 outputs an error to a predetermined error log file (step S604).

The control unit 51 may output an error message to, for example, a person in charge of the manufacturer or a person in charge of the medical institution by any means such as e-mail or short message. The person in charge of the manufacturer takes appropriate measures such as confirming the remanufacturing process and arranging the collection of the endoscope 10. The person in charge of the medical institution takes appropriate measures such as arranging the collection of the endoscope 10 and confirming the installation location of the tag reader 39.

When it is determined that the record extraction succeeds (YES in step S603), the control unit 51 determines whether or not the detection state of the endoscope 10 is normal (step S605). Specifically, the control unit 51 determines whether or not the name of the medical institution recorded in the medical institution name field of the detected record matches the name of the medical institution in which the client 40 is installed. If not match, the control unit 51 determines that the detection state of the endoscope 10 is not normal. In addition, the control unit 51 determines whether or not date is recorded in the collection date field and the date of use field of the detected record. If the date is recorded in either or both of the collection date field and the date of use field, the control unit 51 determines that the detection state of the endoscope 10 is not normal.

If it is determined that the detection state of the endoscope 10 is not normal (NO in step S605), the control unit 51 outputs an error to a predetermined error log file (step S606). The control unit 51 may output an error message to, for example, a person in charge of the information processing system 70 or a person in charge of the medical institution by any means such as e-mail or short message.

If it is determined that the detection state of the endoscope 10 is normal (YES in step S605), after the termination step S604 or after the termination of step S606, the control unit 51 transmits the determination result to the client 40 (step S607). The control unit 41 receives the determination result and records the determination result in the predetermined error log file (step S504).

If it is determined that the endoscope 10 is not a newly detected endo scope 10 (NO in step S502), the control unit 41 determines whether the location of the tag reader 39 where the endoscope 10 is detected is the endoscopic examination room (step S511). If it is determined that the location of the tag reader 39 is the endoscopic examination room (YES in step S511), the control unit 41 records the "inspection room" in the location field of the record extracted from the second endoscope DB 62 (step S512).

If it is determined that the location of the tag reader 39 is not the endoscopic examination room (NO in step S511), the control unit 41 determines whether the location of the tag reader 39 where the endoscope 10 is detected is the collection container 38 (step S513). If it is determined that the endoscope 10 is put into the collection container 38 (YES in step S513), the control unit 41 transmits the endoscope ID and collection request to the server 50 (step S514).

The control unit 51 receives the collection request (step S611). The control unit 51 creates a new record in the collection request DB 65 and records the name of the medical institution where the client 40 transmitting the collection request is installed and the endoscope ID corresponding to the collection request. The control unit 51 sets the arrangement field and the completion field to the initial value "NO" (step S612).

The control unit 41 records the "collection container" in the location field of the record extracted from the second endoscope DB 62 and the date in the date of use field, respectively (step S515). If it is determined that the location of the tag reader 39 is not the collection container 38 (NO in step S513), after the termination of step S504, step S512, or step S515, the control unit 41 determines whether to end the process (step S516). For example, when a termination instruction is received from the administrator, the control unit 41 determines that the process is terminated.

If it is determined that the process is not terminated (NO in step S516), the control unit 41 returns to step S501. If it is determined that the process is not terminated (YES in step S516), the control unit 41 terminates the process.

Note that although the explanation by the flowchart is omitted, when the endoscope 10 is collected from the collection container 38, the control unit 41 records "—" in the location field of the record extracted from the second endoscope DB 62 and the date in the collection date field, respectively.

Figure 12:
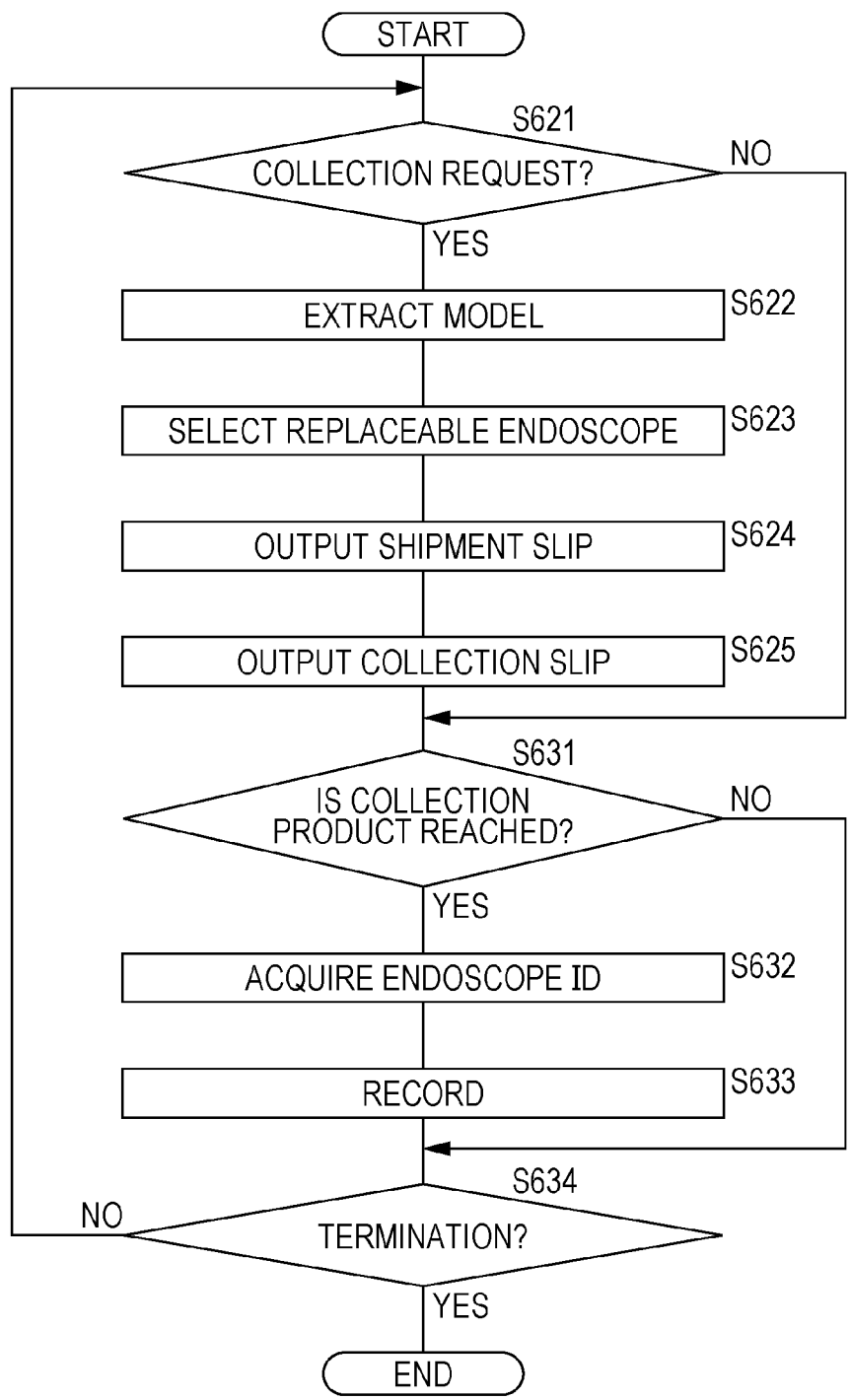
FIG. 12 is a flowchart illustrating a process flow of a program executed by a server.

FIG. 12 is a flowchart illustrating a process flow of a program executed by the server 50. The program illustrated in FIG. 12 may be executed at any time during a time when the load of the control unit 51 is light, and may be executed at a predetermined time. The program illustrated in FIG. 12 may be executed when a new record is added to the collection request DB 65 and when the endoscope 10 collected from the medical institution arrives at the manufacturer.

The program illustrated in FIG. 12 may be executed when a predetermined number of new records are added to the collection request DB 65 and when the endoscope 10 collected from the medical institution arrives at the manufacturer. The program illustrated in FIG. 12 may be executed when a predetermined number of new records are added to the collection request DB 65 based on the collection request received from one medical institution and when the endoscope 10 collected from the medical institution arrives at the manufacturer.

The control unit 51 determines whether a new collection request is recorded in the collection request DB 65 (step S621). Specifically, the control unit 51 searches the collection request DB 65 and extracts records in which "NO" is recorded in the arrangement field. If there is the extracted record, the control unit 51 determines that the collection request is recorded.

If it is determined that a new collection request is recorded (YES in step S621), the control unit 51 searches the first endoscope DB 61 using the endoscope ID recorded in the endoscope ID field of the new record in the collection request DB 65 as a key, and extracts the record. The control unit 51 extracts the model of endoscope 10 for which the collection request has been received from the model name field of the extracted record (step S622).

The control unit 51 searches the first endoscope DB 61 and extracts records in which date is recorded on the sterilization date and date is not recorded on the shipping date. The control unit 51 searches the records extracted using the model extracted in step S622 as a key, and extracts the endoscope 10 of the same model that has not been shipped after the sterilization. The control unit 51 selects one of the extracted records. The control unit 51 acquires the endoscope ID recorded in the endoscope ID field of the selected record. As a result, the replaceable endoscope 10 is selected from the first endoscope DB 61 (step S623).

Note that the control unit 51 may search the first endoscope DB 61, and extract records in which date is recorded on the assembly completion date and date is not recorded on the sterilization date. By performing the sterilization of the endoscope 10 after defining the shipping destination, the endoscope 10 with a long sterilization expiration date can be provided to the medical institution.

The control unit 51 outputs the shipping slip of the endoscope 10 selected in step S623 (step S624). Specifically, the control unit 51 adds a new record to the slip DB 66. The control unit 51 records the endoscope ID of the endoscope 10 selected in step S623 in the endoscope ID field of the added record. Similarly, the control unit 51 records the location where the replaceable endoscope 10 was stored in the departure location field and records the medical institution to which the replacement request was transmitted in the destination field. The initial values of the departure date and time field and the arrival date and time field are blank.

The control unit 51 outputs the collection slip of the endoscope 10 for which the collection request has been received in step S621 (step S625). Specifically, the control unit 51 adds a new record to the slip DB 66. The control unit 51 records the endoscope ID of the endoscope 10 selected in step S623 in the endoscope ID field of the added record. Similarly, the control unit 51 records the location where the replaceable endoscope 10 was stored in the departure location field and records the medical institution to which the replacement request was transmitted in the destination field. The initial values of the departure date and time field and the arrival date and time field are blank.

Note that when a plurality of collection requests are extracted in step S621, the control unit 51 sequentially repeats the processes from step S622 to step S625, and outputs a shipping slip and a collection slip for each endoscope 10. By the processing from step S622 to step S625, the control unit 51 collects the used endoscope 10 and outputs a replacement instruction to deliver the non-used endoscope 10.

If it is determined that no new collection request has been recorded (NO in step S621), or after the termination of step S625, the control unit 51 determines if the collected endoscope 10 has arrived at the manufacturer (step S631). If it is determined that the collected endoscope 10 has arrived (YES in step S631), the control unit 51 acquires the endoscope ID of the collected endoscope 10 (step S632).

The control unit 51 searches the first endoscope DB 61 using the acquired endoscope ID as a key and extracts a record. The control unit 51 records the collection date in the collection date field of the extracted record (step S633).

Note that when a plurality of endoscopes 10 have arrived in step S631, the control unit 51 sequentially repeats the processes from step S632 to step S633, and records the collection of each endoscope 10 in the first endoscope DB 61.

If it is determined that the collected endoscope 10 has not arrived at the manufacturer (NO in step S631), or after the termination of step S633, the control unit 51 determines whether or not to terminate the process (step S634). If it is determined that the process is not terminated (NO in step S634), the control unit 51 returns to step S621. If it is determined that the process is terminated (YES in step S634), the control unit 51 terminates the process.

Figures 13, 14:
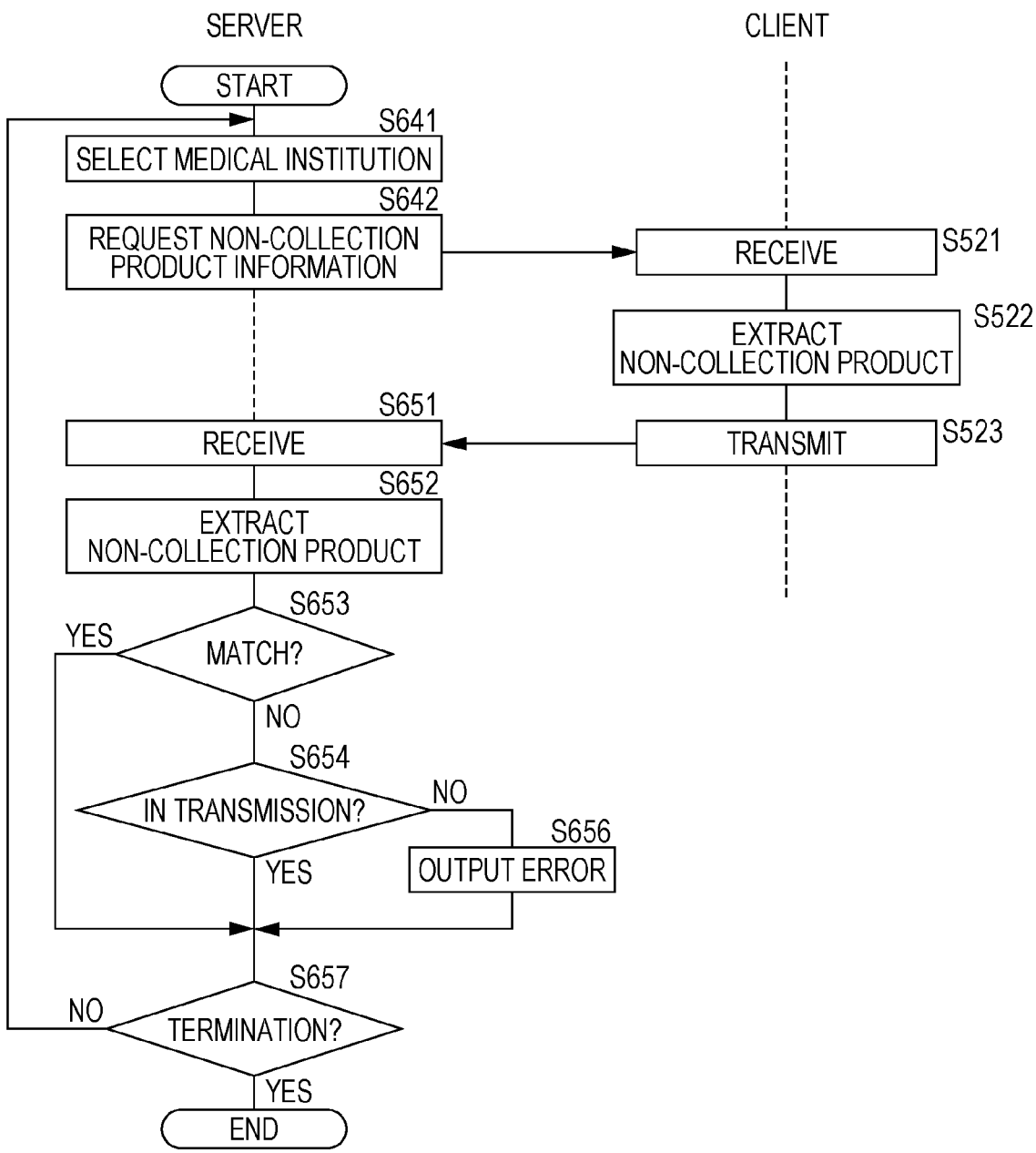
FIG. 13 is a flowchart for explaining a process flow of a program that performs inventory.
FIG. 14 is an explanatory diagram for explaining a record layout of an inspection schedule DB.

FIG. 13 is a flowchart for explaining a process flow of a program that performs inventory. The program illustrated in FIG. 13 is executed periodically, for example, once a day or once a week.

The control unit 51 selects the medical institution to be processed (step S641). The control unit 51 requests the client 40 installed in the selected medical institution for information on the non-collected products (step S642).

The control unit 41 receives the request (step S521). The control unit 41 searches the second endoscope DB 62, and extracts records in which a date is not recorded in the collection date field (step S522). The control unit 41 transmits, to the server 50, the endoscope ID recorded in the endoscope ID field of the extracted record (step S523).

The control unit 51 receives the endoscope ID, and temporarily stores the endoscope ID in the main storage device 52 or the auxiliary storage device 53 (step S651). The control unit 51 searches the first endoscope DB 61 using the name of the medical institution of the medical institution selected in step S641 using a key, and extracts the record. In addition, the control unit 51 extracts the record in which collection date is not recorded, that is, the record of the non-collected products (step S652).

The control unit 51 collates the endoscope ID received in step S651 with the endoscope ID recorded in the endoscope ID field of the record extracted in step S652, and determines whether or not these endoscope IDs match (step S653).

If it is determined that these endoscope IDs do not match (NO in step S653), the control unit 51 determines whether the endoscope 10 corresponding to the mismatched endoscope ID is being transported (step S654). Specifically, the control unit 51 searches the slip DB 66 using the mismatched endoscope ID as a key, and extracts the records. If the date and time are recorded in the departure date and time field of the extracted record and the date and time are not recorded in the arrival date and time field, the control unit 51 determines that the endoscope 10 corresponding to the endoscope ID is being transported. If it is determined to be other than that, the control unit 51 determines that the endoscope 10 corresponding to the endoscope ID is not being transported.

If it is determined that the endoscope 10 is not being transported (NO in step S654), the control unit 51 outputs an error to a predetermined error log file (step S656). The control unit 51 may output an error message to, for example, a person in charge of the manufacturer or a person in charge of the medical institution by any means such as e-mail or short message. A person in charge takes appropriate measures such as searching for the mismatched endoscope 10 and correcting the inconsistency of the DB.

If it is determined that the endoscope IDs match (YES in step S653), if it is determined that the endoscope is being transported (YES in step S654), or after the termination of step S656, the control unit 51 determines whether the processes for all the medical institutions are terminated (step S657). If it is determined that the process is not terminated (NO in step S657), the control unit 51 returns to step S641. If it is determined that the process is terminated (YES in step S657), the control unit 51 terminates the process.

Although the description of the flowchart is omitted, the control unit 51 regularly calculates the fee charged to the medical institution. Specifically, the number of endoscopes 10 replaced for each medical institution is acquired from the first endoscope DB 61, and the charge is calculated based on Equation (1). The manufacturer will issue an invoice to the medical institution based on the calculated fee. Note that the control unit 51 may automatically transmit an invoice to the medical institution based on the calculated fee.

According to the first embodiment, it is possible to provide the information processing system 70 that reduces the burden on the health-care personnel engaging in the endoscopic examination. Since the reusable parts are reused, the cost of the single-use endoscope 10 can be reduced and the amount of waste can be reduced.

Since the first endoscope DB 61 records the endoscope ID and the part ID of the reusable part in association with each other, it is possible to provide the information processing system 70 that can ensure the traceability of the parts used in the remanufactured endoscope 10.

Since the first endoscope DB 61 and the second endoscope DB 62 do not record the information on the patient such as the patient ID, it is possible to provide the information processing system 70 without risk of leakage of personal information. Note that by recording the endoscope ID of the endoscope 10 used for each patient in the electronic medical chart system, it is possible to ensure traceability of which patient the endoscope 10 is used for, if necessary.

In the first embodiment, the flexible endoscope 10 has been described as an example, but the endoscope 10 may be a hard mirror. The endoscope 10 may be an industrial endoscope. It is possible to provide an industrial endoscope that can be used in places where sterilization is required, such as a pipeline in a food factory.

By using short-range wireless communication such as RFID for the endoscope tag 18 and the tag reader 39, it is possible to provide the information processing system 70 that reads and records the endoscope ID simply by moving the endoscope 10 to a predetermined location.

By sharing information with logistics companies using the slip DB 66, it is possible to provide the information processing system 70 that automatically performs instructions for shipping and delivery. At a logistics company or the like, for example, the endoscope 10 may be mixed and transported with other medical devices and pharmaceuticals. The vehicle that collects the used endoscope 10 and the vehicle that delivers the replaceable endoscope 10 may be different vehicles.

Since the endoscope 10 is not reprocessed, chemicals such as disinfectants and water for cleaning are not used in each medical institution. If the manufacturer is well-equipped, the water used for cleaning can be sterilized and reused, so the environmental load when cleaning the endoscope 10 can be reduced.

Since the endoscope 10 is disassembled after being used by the manufacturer, each non-reusable part that constitutes the endoscope 10 can be appropriately separated and discarded. From the above, it is possible to provide the endoscope 10 with less environmental load.

Second Embodiment

A second embodiment relates to an information processing system 70 that acquires an inspection schedule from an in-hospital system such as an electronic medical chart system or a medical appointment system and automatically delivers a necessary endoscope 10. The description of the parts common to the first embodiment will be omitted.

FIG. 14 is an explanatory diagram for explaining a record layout of an inspection schedule DB. The inspection schedule DB is a DB that records a scheduled inspection date and a model name of the endoscope 10 used for inspection in association with each other. The inspection schedule DB has a scheduled inspection date field and a model name field. The scheduled inspection date field records the scheduled inspection date. The model name field records the model name of the endoscope 10.

FIG. 15 is an explanatory diagram for explaining a record layout of a margin DB. The margin DB is a DB that records a name of a medical institution in association with a margin of endoscope 10 that is determined in advance based on the contract.

The margin DB has a medical institution name field and a margin field. The margin field has subfields for each model of the endoscope 10, such as "E001", "E002", and "E003". The medical institution name field records the name of the medical institution. Each subfield of the margin field records the margin for each model of the endoscope 10 defined based on the contract with each medical institution.

Here, the margin means the number of endoscopes 10 that have no specific schedule to be used for inspection. Each medical institution sets a margin and makes a contract with a manufacturer in preparation for unplanned endoscopic examination such as emergency endoscopic examination. The margin DB has one record for one medical institution.

Figure 16:
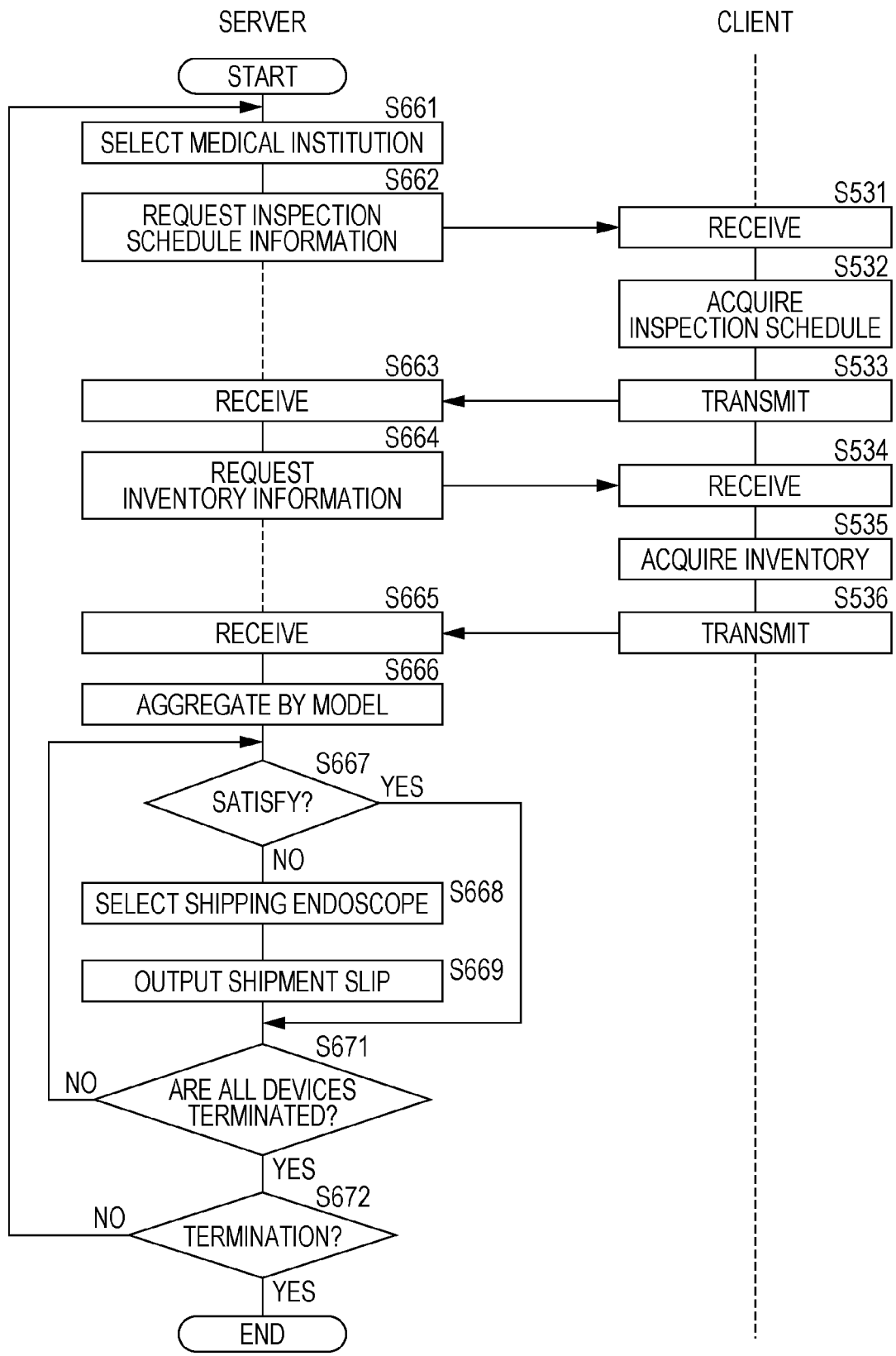
FIG. 16 is a flowchart for explaining a process flow of a program according to a second embodiment.

FIG. 16 is a flowchart for explaining a process flow of a program according to a second embodiment. The program illustrated in FIG. 16 is regularly executed, for example, at a predetermined time in the morning and evening.

The control unit 51 selects the medical institution to be processed (step S661). The control unit 51 requests the client 40 installed in the selected medical institution for information on the schedule of the endoscopic examination (step S662).

The control unit 41 receives the request (step S531). The control unit 41 requests information from the in-hospital system based on a predetermined protocol and acquires the inspection schedule DB described using FIG. 14 (step S532). The control unit 41 transmits the data recorded in the inspection schedule DB to the server 50 (step S533).

The control unit 51 receives data recorded in the inspection schedule DB, and temporarily stores the data in the main storage device 52 or the auxiliary storage device 53 (step S663). The control unit 51 requests the client 40 for information on the inventory of the endoscope 10 (step S664).

The control unit 41 receives the request (step S534). The control unit 41 acquires the inventory of the endoscope 10 stored in the equipment room from the second endoscope DB 62 (step S535). Specifically, the control unit 41 searches the second endoscope DB 62 and extracts the record in which the "equipment room" is described in the location field. The control unit 41 transmits a list of model names recorded in the model name field of the extracted record to the server 50 (step S536).

The control unit 51 receives the list of the model names (step S665). The control unit 51 aggregates the inspection schedule received in step S663 and the inventory received in step S665, respectively, for each model (step S666).

The control unit 51 selects the model to be determined. The control unit 51 determines whether or not the inventory quantity of the model to be determined satisfies the margin for each medical institution recorded in the margin DB described with reference to FIG. 15 (step S667). Specifically, the control unit 51 determines whether or not Equation (2) is satisfied for each model.

$$\text{Inventory quantity} > \text{inspection schedule quantity} + \text{margin} \quad (2)$$

If it is determined that Equation (2) is not satisfied (NO in step S667), the control unit 51 searches the first endoscope DB 61 and extracts the endoscope 10 of the same model that is not shipped after the sterilization. The control unit 51 selects one of the extracted records, and acquires the endoscope ID recorded in the endoscope ID field. As a result, the shippable endoscope 10 is selected from the first endoscope DB 61 (step S668).

The control unit 51 outputs the shipping slip of the endoscope 10 (step S669). Note that in step S668 and step S669, the control unit 51 may select a predetermined number of endoscopes 10 in shipping units set in advance and output a shipping slip. For example, the delivery frequency of the endoscope 10 can be reduced by setting the shipping unit to 5 units or 10 units.

If it is determined that Equation (2) is satisfied (YES in step S667), or after the termination of step S669, the control unit 51 determines whether or not the processes of all models are terminated (step S671). If it is determined that the process is not terminated (NO in step S671), the control unit 51 returns to step S667.

If it is determined that the process is terminated (YES in step S671), the control unit 51 determines whether or not the process of all medical institutions is terminated (step S672). If it is determined that the process is not terminated (NO in step S672), the control unit 51 returns to step S661. If it is determined that the process is terminated (YES in step S672), the control unit 51 terminates the process.

Figure 17:
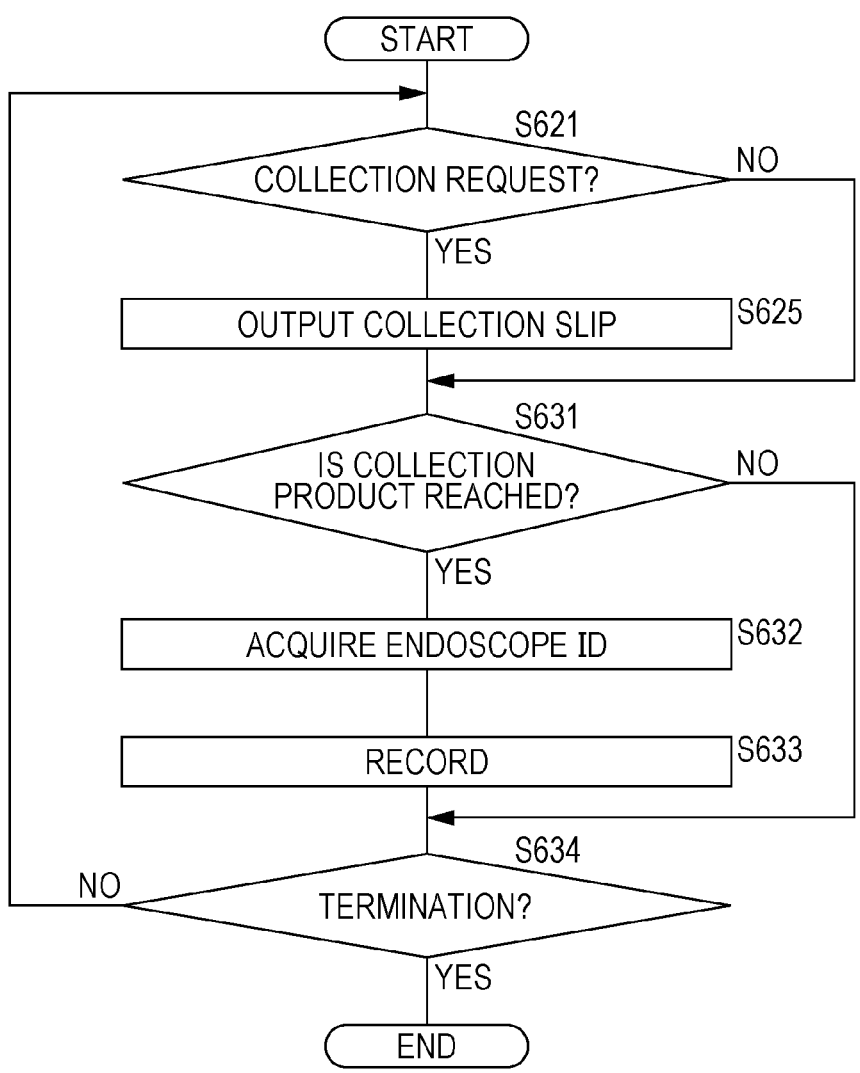
FIG. 17 is a flowchart for explaining a process flow of a program executed by a server according to the second embodiment.

FIG. 17 is a flowchart for explaining a process flow of the program executed by the server 50 according to the second embodiment. The program illustrated in FIG. 17 may be executed at any time during a time when the load of the control unit 51 is light, or may be executed at a predetermined time. The program illustrated in FIG. 17 may be executed when a new record is added to the collection request DB 65 and when the endoscope 10 collected from the medical institution arrives at the manufacturer.

The control unit 51 determines whether a new collection request is recorded in the collection request DB 65 (step S621). Specifically, the control unit 51 searches the collection request DB 65 and extracts records in which "NO" is recorded in the arrangement field. If there is the extracted record, the control unit 51 determines that the collection request is recorded.

If it is determined that a new collection request is recorded (YES in step S621), the control unit 51 outputs the collection slip of the endoscope 10 for which the collection request has been received in step S621 (step S625). Specifically, the control unit 51 adds a new record to the slip DB 66. The control unit 51 records the endoscope ID of the endoscope 10 selected in step S623 in the endoscope ID field of the added record. Similarly, the control unit 51 records the location where the replaceable endoscope 10 was stored in the departure location field and records the medical institution to which the replacement request was transmitted in the destination field. The initial values of the departure date and time field and the arrival date and time field are blank.

Note that when the plurality of collection requests are extracted in step S621, the control unit 51 repeats the processes up to step S625, and outputs the collection slip for each endoscope 10.

If it is determined that no new collection request has been recorded (NO in step S621), or after the termination of step S625, the control unit 51 determines if the collected endoscope 10 has arrived at the manufacturer (step S631). If it is determined that the collected endoscope 10 has arrived (YES in step S631), the control unit 51 acquires the endoscope ID of the collected endoscope 10 (step S632).

The control unit 51 searches the first endoscope DB 61 using the acquired endoscope ID as a key and extracts a record. The control unit 51 records the collection date in the collection date field of the extracted record (step S633).

Note that when a plurality of endoscopes 10 have arrived in step S631, the control unit 51 sequentially repeats the processes from step S632 to step S633, and records the collection of each endoscope 10 in the first endoscope DB 61.

If it is determined that the collected endoscope 10 has not arrived at the manufacturer (NO in step S631), or after the termination of step S633, the control unit 51 determines whether or not to terminate the process (step S634). If it is determined that the process is not terminated (NO in step S634), the control unit 51 returns to step S621. If it is determined that the process is terminated (YES in step S634), the control unit 51 terminates the process.

According to the second embodiment, it is possible to provide the information processing system 70 that can smoothly perform the necessary endoscopic examination with the necessary minimum margin even in the medical institution where the number of endoscopic examinations fluctuates greatly. Since the margin required for the margin DB is recorded, when the emergency endoscopic examination is required, delivery is delayed due to traffic congestion, or other unexpected events occur, it is possible to provide the information processing system 70 that does not cause the shortage of the endoscope 10.

Third Embodiment

A third embodiment relates to an endoscope 10 in which a light emitting element 136 is built in a distal tip portion 13. The description of the parts common to the first embodiment will be omitted.

Figure 18:
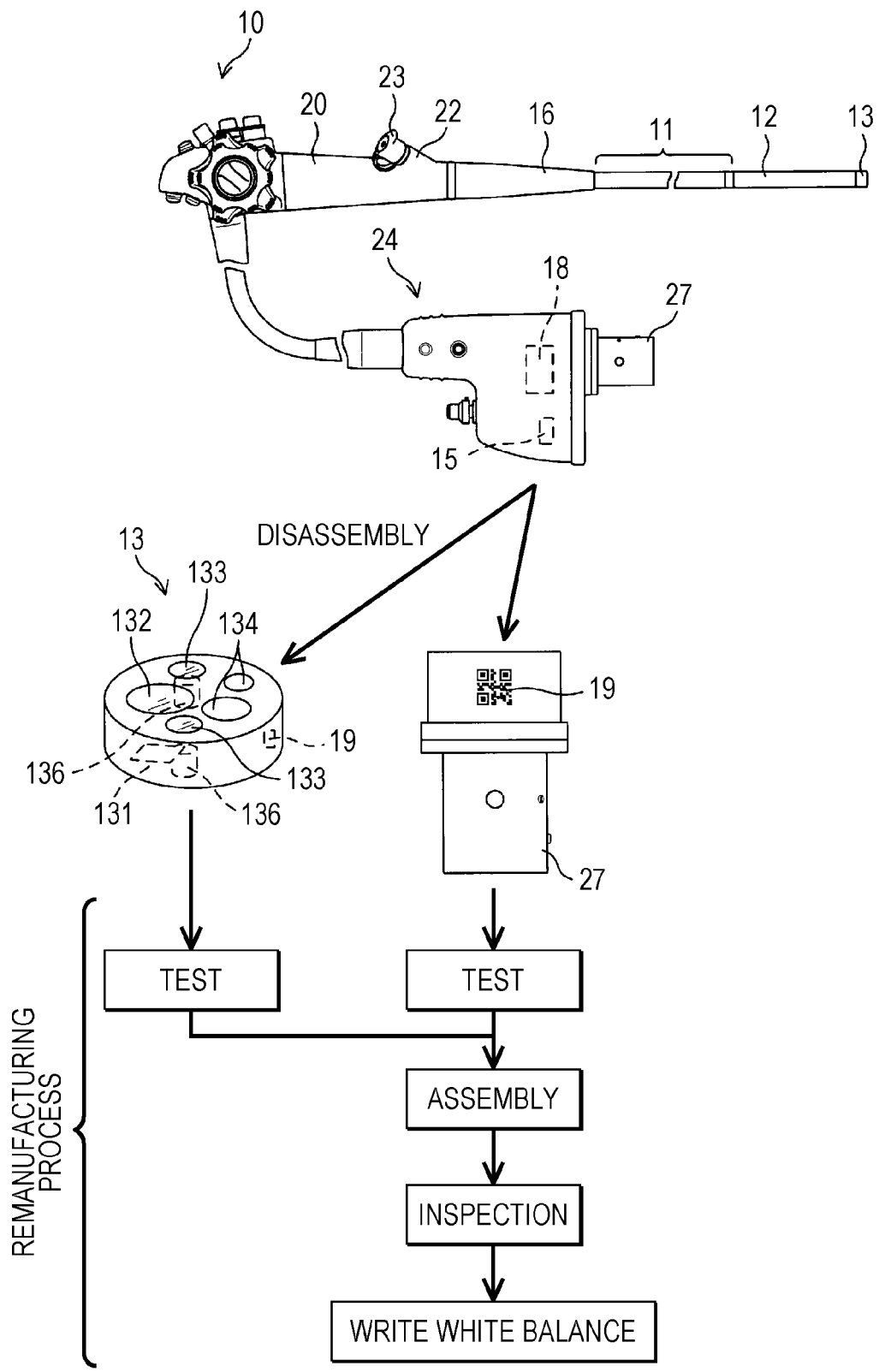
FIG. 18 is a flowchart for explaining a remanufacturing process of an endoscope according to a third embodiment.

FIG. 18 is a flowchart for explaining a remanufacturing process of an endoscope 10 according to a third embodiment. In the third embodiment, the case where the distal tip portion 13 and a scope connector 27 are reusable parts will be described as an example.

The endoscope 10 is disassembled according to a predetermined procedure. The non-reusable part is discarded. The reusable part in the first embodiment will be described.

The distal tip portion 13 is a disk shape provided with a through hole 134 penetrating in a thickness direction, and has an observation window 132 and two illumination windows 133 on one surface. The observation window 132 and the illumination window 133 are covered with a transparent plate such as plastic or glass.

An image sensor 131 and a lens on which an optical image on the surface of the image sensor 131 is formed are arranged inside the observation window 132. The light emitting element 136 such as a light emitting diode (LED) is arranged in an illumination window 133. An illumination lens may be provided between the light emitting element 136 and the illumination window 133 to dissipate the light emitted from the light emitting element 136 at an appropriate emission angle. The image sensor 131 captures an image of an object illuminated by the light emitted from the illumination window 133 through the observation window 132.

The distal tip portion 13 is provided with a through hole 134 that penetrates in the thickness direction. Furthermore, a part tag 19 in which a part ID uniquely assigned to each reusable part is recorded is embedded in the distal tip portion 13. The part tag 19 is constituted by, for example, a small wireless chip.

A predetermined quality test is performed on each reusable part taken out from the endoscope 10. The reusable part that accepts the quality inspection and the new non-reusable part are combined to assemble a new endoscope 10. A predetermined quality inspection is performed on the assembled endoscope 10.

The white balance is adjusted for the endoscope 10 that accepts the inspection. The adjustment result is written into the memory element 15 such as the IC chip built in the connector unit 24. When the storage capacity of the endoscope tag 18 is sufficient, the endoscope tag 18 may also serve as the memory element 15.

When the endoscope 10 of the third embodiment is connected to a processor 32 for endoscope, the white balance adjustment result written into the memory element 15 is read into the processor 32 for endoscope. Therefore, it is possible to provide the endoscope 10 that does not require the white balance adjustment before use.

When the signal line and the electrode line connected to the image sensor 131 have little effect on the white balance, the memory element 15 into which the white balance is written may be built in the distal tip portion 13. In this way, there is no need to adjust the white balance each time the endoscope 10 is assembled.

According to the third embodiment, it is possible to the endoscope 10 in which the light emitting element 136 is built in the distal tip portion 13. Since the endoscope 10 does not have the relatively expensive light guide 29 and light guide connector 28, it is possible to provide an inexpensive endoscope 10.

Fourth Embodiment

A fourth embodiment relates to an information processing system 70 that replaces an endoscope 10 after a predetermined period of time after being sterilized. The description of the parts common to the first embodiment will be omitted.

Figure 19:
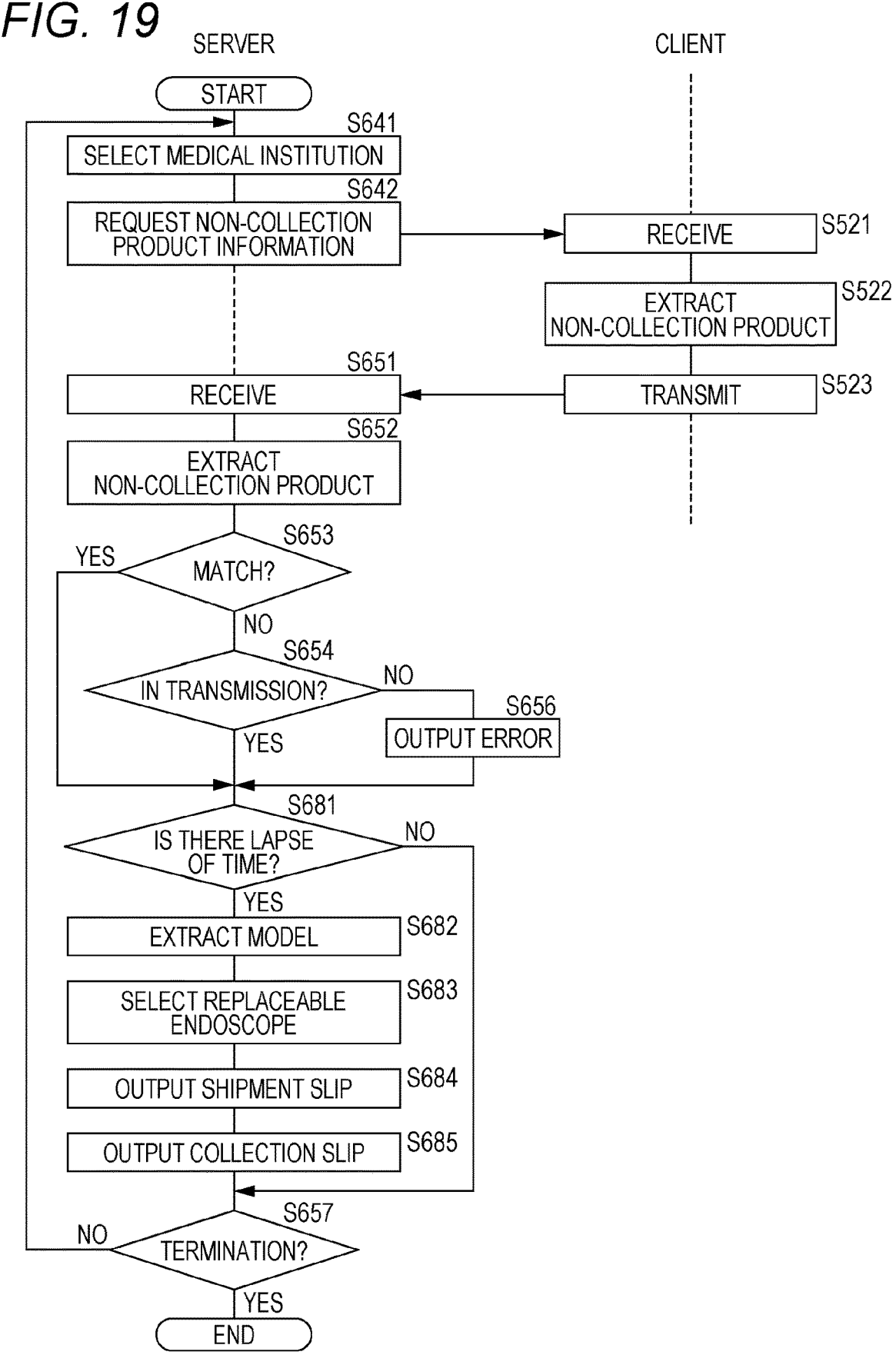
FIG. 19 is a flowchart for explaining a process flow of a program according to a fourth embodiment.

FIG. 19 is a flowchart for explaining a process flow of a program according to a fourth embodiment. The program illustrated in FIG. 19 is a program used in place of the program described with reference to FIG. 13. Since the processes up to step S656 are the same as the program described with reference to FIG. 13, a description thereof will be omitted.

If it is determined that endoscope IDs match (YES in step S653), if it is determined that the endoscope is being transported (YES in step S654), or after the termination of step S656, the control unit 51 searches a sterilization date field of the record of the non-collected product extracted in step S652 and determines whether or not the endoscope 10 whose predetermined period of time has passed from the sterilization date is included (step S681). The predetermined period is set to be slightly shorter than the predetermined effective period of sterilization.

When it is determined that there is an endoscope 10 whose period has passed (YES in step S681), the control unit 51 extracts the model of the endoscope 10 from the model name field of the corresponding record (step S682). The control unit 51 searches the first endoscope DB 61 and extracts the endoscope 10 of the same model that is not shipped after the sterilization. The control unit 51 selects one of the extracted records, and acquires the endoscope ID recorded in the endoscope ID field. As a result, the replaceable endoscope 10 is selected from the first endoscope DB 61 (step S683).

The control unit 51 outputs the shipping slip that ships the replaceable endoscope 10 (step S684). The control unit 51 outputs the collection slip of the endoscope 10 determined that the predetermined period has elapsed in step S681 (step S685).

Note that when the plurality of endoscopes 10 whose period has passed are extracted in step S681, the control unit 51 sequentially repeats the processes from step S682 to step S685, and outputs a shipping slip and a collection slip for each endoscope 10.

If it is determined that there is no endoscope 10 whose period has passed (NO in step S681) or after the termination of step S685, the control unit 51 determines whether the process for all medical institutions is terminated (step S657). If it is determined that the process is not terminated (NO in step S657), the control unit 51 returns to step S641. If it is determined that the process is terminated (YES in step S657), the control unit 51 terminates the process.

According to the fourth embodiment, it is possible to provide the information processing system 70 for promptly replacing the endoscope 10 whose the sterilization period has expired.

Fifth Embodiment

A fifth embodiment relates to an information processing system 70 that prevents an unauthorized use of an endoscope 10. The description of the parts common to the first embodiment will be omitted.

A processor 32 for endoscope of a fifth embodiment acquires an endoscope ID from an endoscope tag 18 and transmits the acquired ID to a client 40 when the endoscope 10 is connected. When receiving approval from the client 40, the processor 32 for endoscope initiates an operation required for endoscopic examination.

Figure 20:
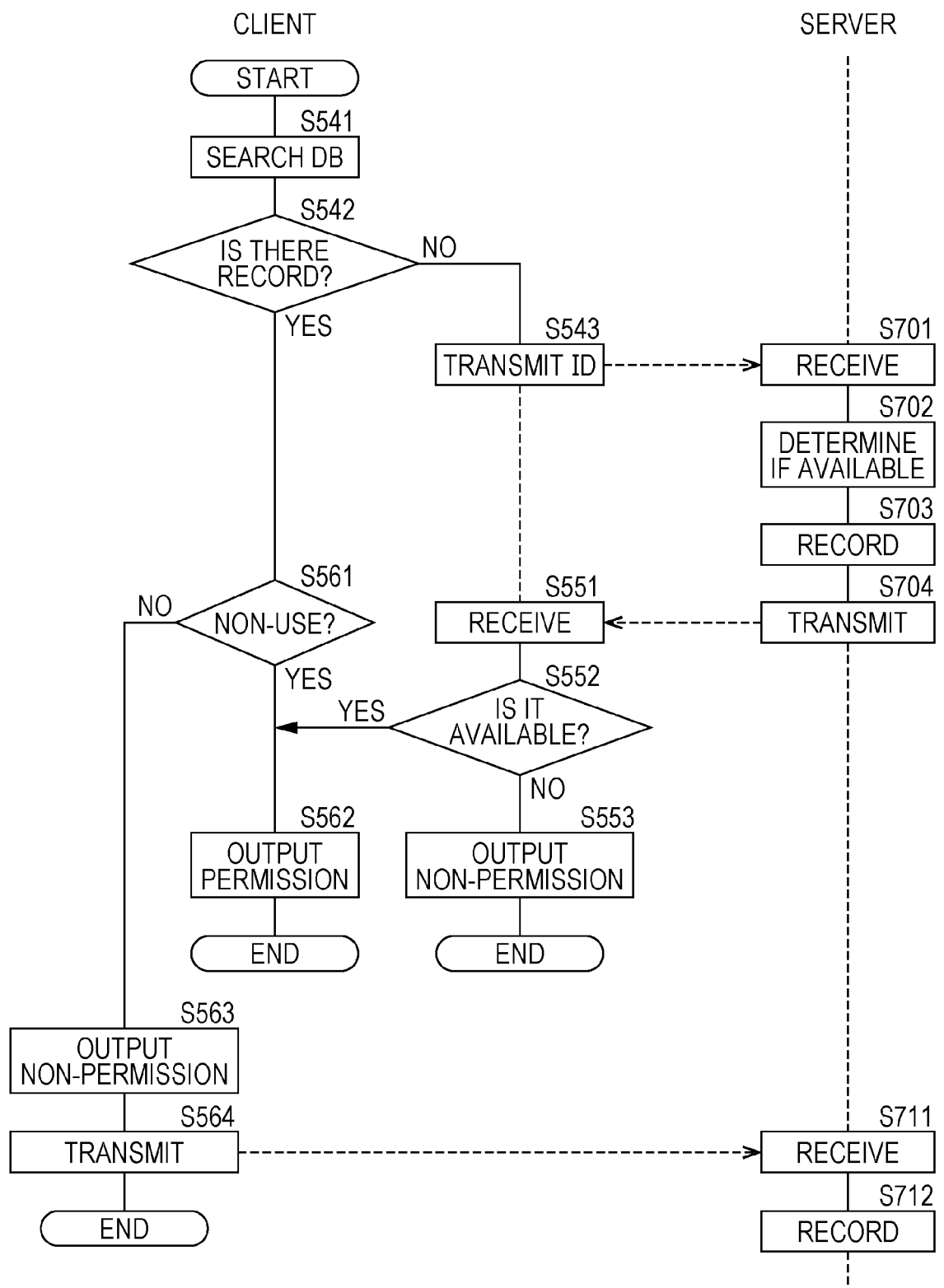
FIG. 20 is a flowchart illustrating a process flow of a program that operates by a client when an endoscope is connected to a processor for endoscope according to a fifth embodiment.

FIG. 20 is a flowchart illustrating a process flow of the program that operates by the client 40 when the endoscope 10 is connected to the processor 32 for endoscope according to the fifth embodiment. The control unit 41 searches the second endoscope DB 62 using the endoscope ID received from the processor 32 for endoscope as a key and extracts the record (step S541).

The control unit 41 determines if there are any extracted records (step S542). If it is determined that there are no records (NO in step S542), the control unit 41 transmits the endoscope ID to the server 50 (step S543).

The control unit 51 receives the endoscope ID (step S701). The control unit 51 searches the first endoscope DB 61 using the endoscope ID as a key, and determines whether or not the endoscope 10 corresponding to the endoscope ID can be used (step S702).

For example, if the endoscope ID is not recorded in the first endoscope DB 61, since the identity of the endoscope 10 connected to the processor 32 for endoscope is unknown, the control unit 51 determines that the endoscope 10 cannot be used. Even if the first endoscope DB 61 records that the endoscope 10 has been used, that is, the date is recorded in the date of use field, the control unit 51 determines that the endoscope 10 cannot be used.

If the first endoscope DB 61 records that the endoscope 10 has been delivered to another medical institution, that is, if the medical institution name field records another medical institution name, it is considered to be mis-delivery. The control unit 51 may determine that the endoscope 10 can be used. This is because it is not desirable to delay the endoscopic examination because of the mis-delivery.

The control unit 51 records the determination result in the predetermined error log file (step S703). The control unit 51 records the determination result to the client 40 (step S704).

The control unit 41 receives the determination result (step S551). The control unit 41 determines according to the received determination result whether the endoscope 10 can be used (step S552). If it is determined according to the received determination result that the endoscope 10 cannot be used (NO in step S552), the control unit 41 transmits to the processor 32 for endoscope that the use of endoscope 10 is not approved (step S553). The processor 32 for endoscope displays an error message on the display device 33 and prompts a user to replace the endoscope 10. The control unit 41 terminates the process.

If it is determined that there is a record (YES in step S542), the control unit 41 determines whether there is a non-used endoscope 10 (step S561). If it is determined that the endoscope 10 is not used, the date is not recorded in the date of use field of the extracted record.

If it is determined that the endoscope 10 is not used (YES in step S561) or if it is determined that the endoscope 10 can be used (YES in step S552), the control unit 41 transmits to the processor 32 for endoscope that the endoscope 10 is approved to use (step S562). The processor 32 for endoscope starts the operation required for the endoscopic examination. The control unit 41 terminates the process.

If it is determined that the endoscope 10 is not unused (NO in step S561), the control unit 41 transmits to the processor 32 for endoscope that the use of endoscope 10 is not approved (step S563). The processor 32 for endoscope displays an error message on the display device 33 and prompts a user to replace the endoscope 10.

The control unit 41 transmits a notification to the server 50 that the reuse of the endoscope 10 is attempted (step S564). The control unit 51 receives the endoscope ID (step S711). The control unit 51 records the notified information in the predetermined error log file (step S712). The log file is used for trouble analysis at a later date, or the like.

The log file is used for trouble analysis at a later date, or the like. It is desirable to prevent the recurrence by performing measures such as allowing users who try to reuse the used endoscope 10 to perform re-instruction on how to use the endoscope 10 or recommending the replacement with the re-processable endoscope system 30.

When the control unit 41 determines that there is no record extracted from the second endoscope DB 62 (NO in step S542), the control unit 41 may automatically output the disapproval without waiting for the determination result from the server 50. By refusing to use the endoscope 10 without normal records, it is possible to provide the information processing system 70 that prevents work mistakes and frauds.

According to the fifth embodiment, it is possible to provide the information processing system 70 that prevents the unauthorized use of the endoscope 10.

Sixth Embodiment

A sixth embodiment relates to an endoscope 10 having an endoscope tag 18 provided in a housing container 71 which is a packing material. The description of the parts common to the first embodiment will be omitted.

Figure 21:
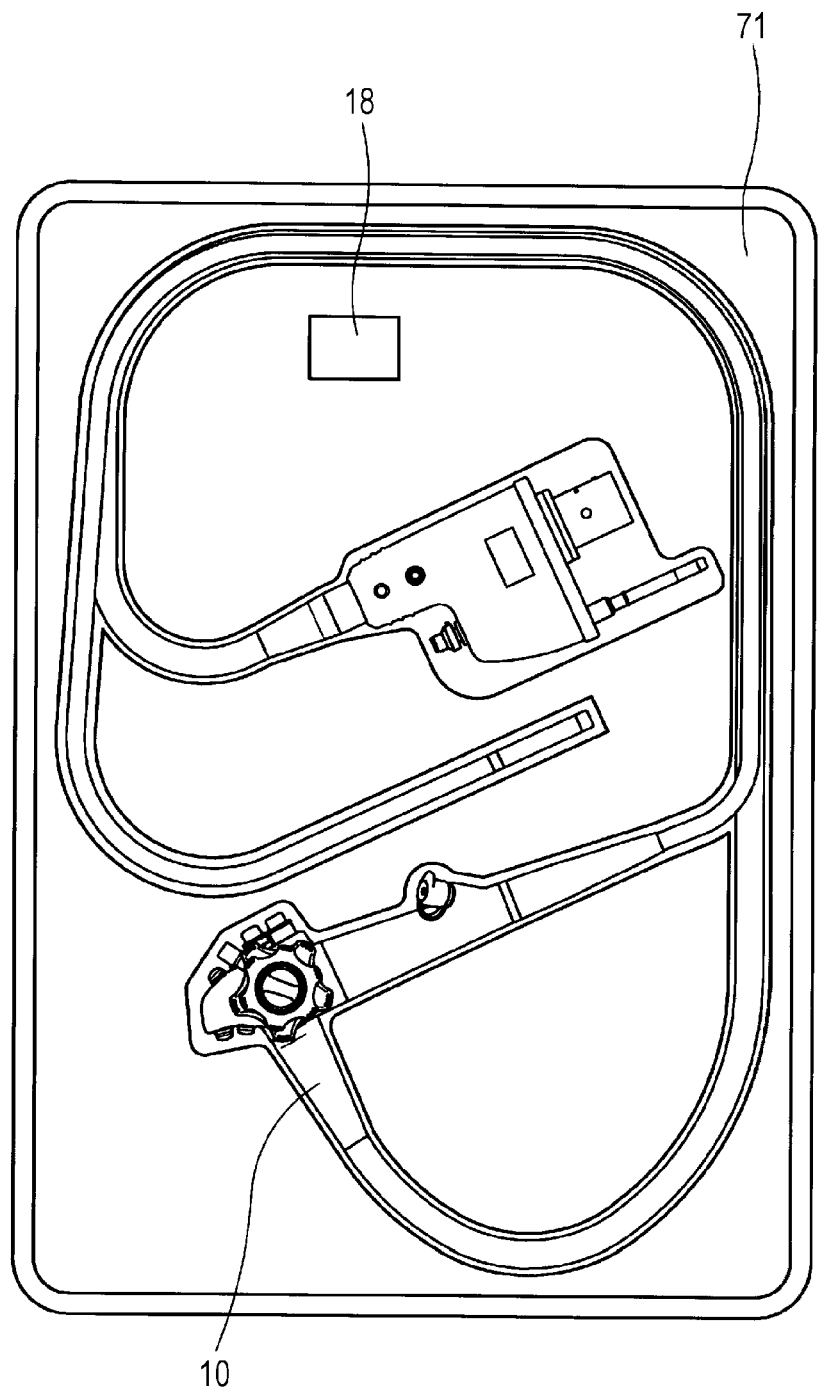
FIG. 21 is a flowchart for explaining a packing state of an endoscope according to a sixth embodiment.

FIG. 21 is a flowchart for explaining a packing state of an endoscope 10 according to a sixth embodiment. The endoscope 10 is individually housed in a housing container 71 provided with a recess matching the shape of the endoscope 10 by press molding or the like. The completed endoscope 10 is enclosed in a sterilization pack together with the housing container 71, and is sterilized by, for example, electron beam sterilization and the like. The housing container 71 may also serve as a sterilization pack. The endoscope tag 18 is attached to the housing container 71.

According to the sixth embodiment, since a large size endoscope tag 18 can be used, the number of digits of the endoscope ID can be increased even when a two-dimensional bar code is used for the endoscope tag 18, for example.

When the endoscope tag 18 is attached to the housing container 71, it is desirable that the used endoscope 10 is put into the collection container 38 while the used endoscope 10 is housed in the housing container 71 again. Therefore, it is desirable that the housing container 71 has a shape that allows the user to easily house the used endoscope 10.

Seventh Embodiment

Figure 22:
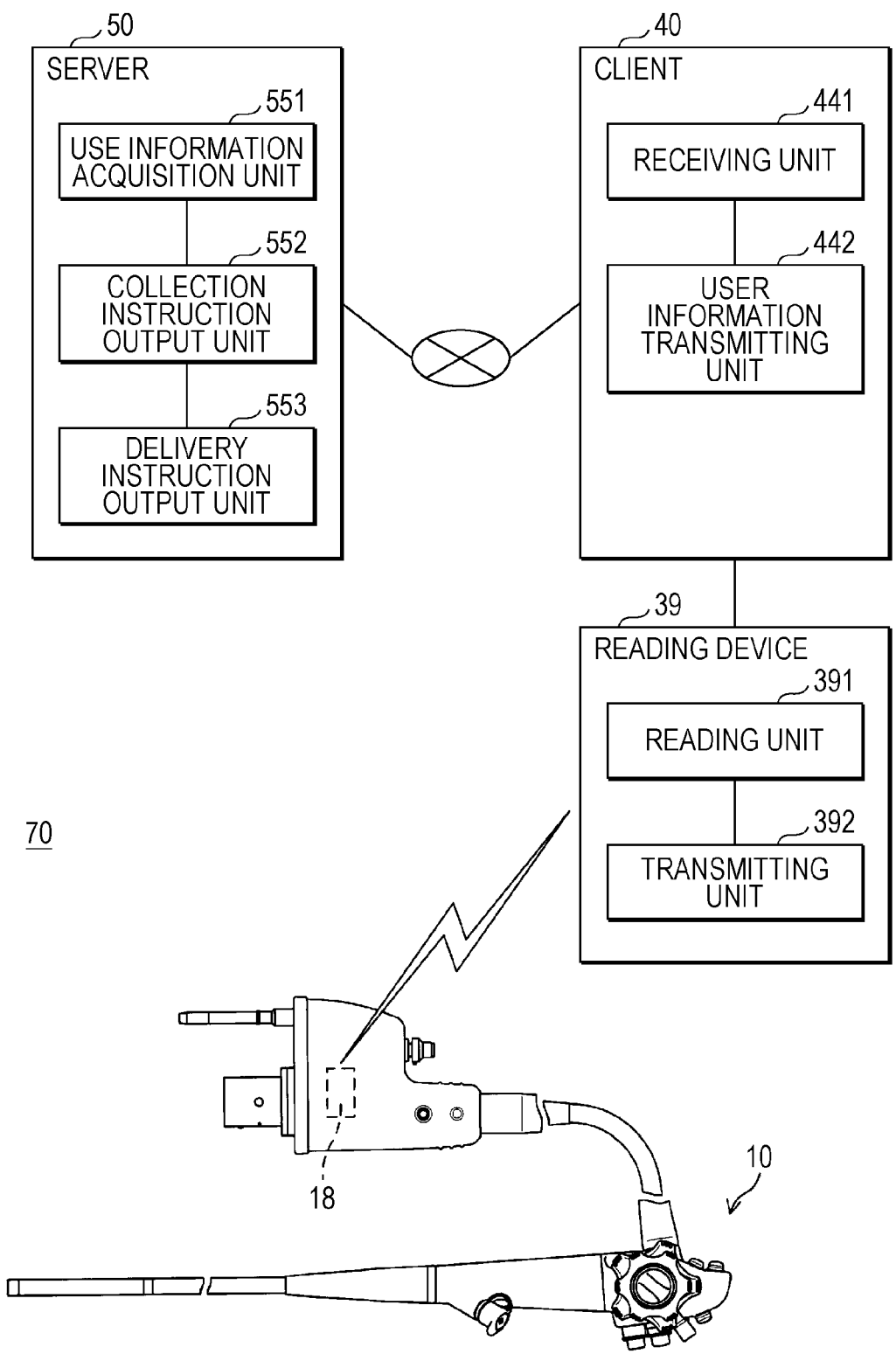
FIG. 22 is a functional block diagram of an information processing system according to a seventh embodiment.

FIG. 22 is a functional block diagram of an information processing system 70 according to a seventh embodiment. The information processing system 70 includes a server 50, a client 40 connected to the server 50 via a network, and a reading device 39 connected to the client 40.

The reading device 39 includes a reading unit 391 and a transmitting unit 392. The reading unit 391 reads an endoscope ID assigned to a single-use endoscope 10. The transmitting unit 392 transmits the endoscope ID read by the reading unit 391 to the client 40.

The client 40 includes a receiving unit 441 and a use information transmitting unit 442. The receiving unit 441 receives the endoscope ID transmitted from the transmitting unit 392. The use information transmitting unit 442 transmits the use information on the endoscope 10 based on the endoscope ID received by the receiving unit 441.

The server 50 includes a use information acquisition unit 551, a collection instruction output unit 552, and a delivery instruction output unit 553. The use information acquisition unit 551 acquires the use information transmitted from the use information transmitting unit 442. The collection instruction output unit 552 outputs a collection instruction to collect the endoscope 10 from the medical institution when the use information acquisition unit 551 acquires use information. The delivery instruction output unit 553 outputs the delivery instruction that delivers the non-used replaceable endoscope 10 to the medical institution.

Eighth Embodiment

Figure 23:
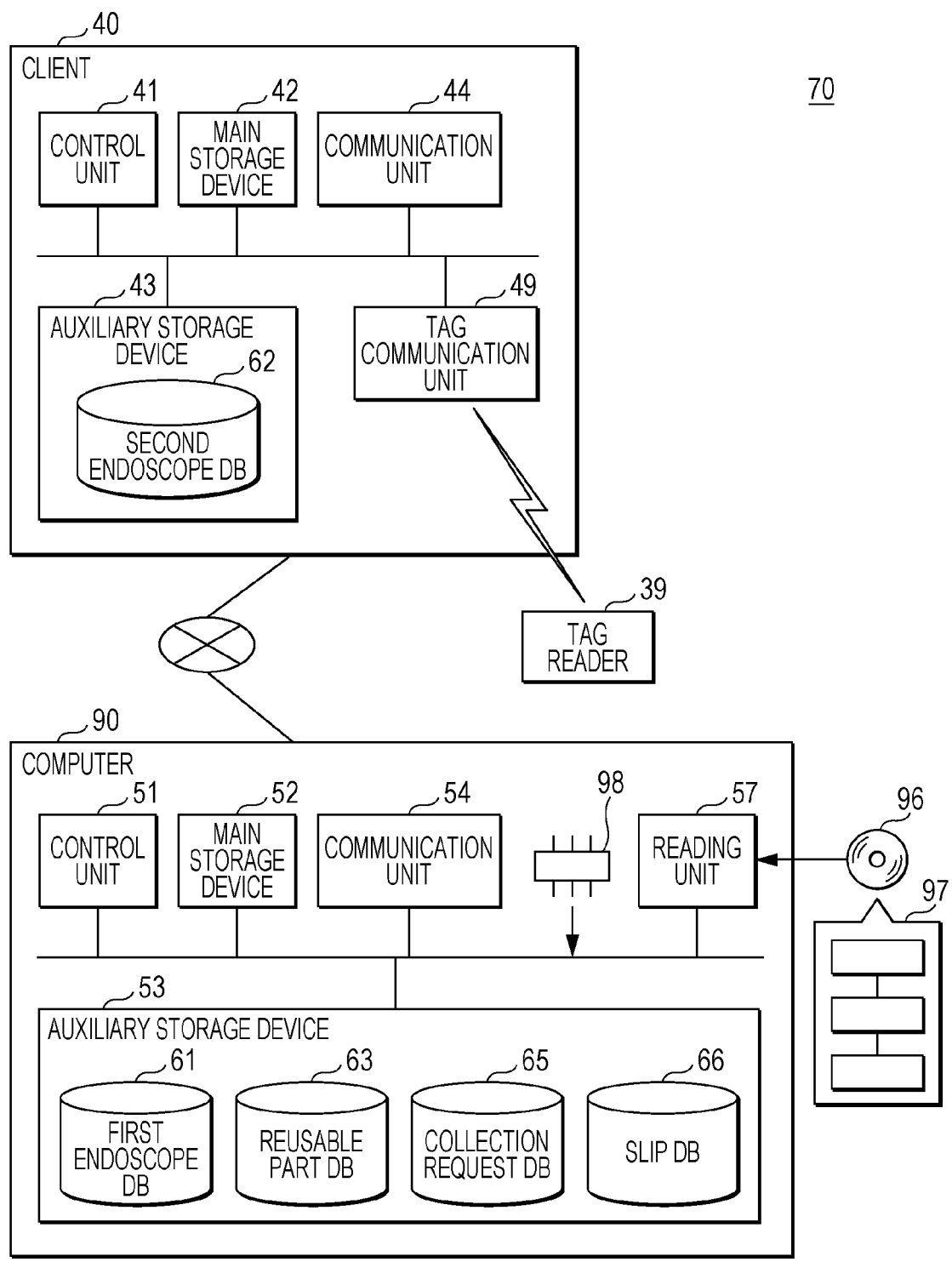
FIG. 23 is an explanatory diagram for explaining a configuration of an information processing system according to an eighth embodiment.

An eighth embodiment relates to an information processing system 70 realized by operating a general-purpose computer 90 and a program 97 in combination. FIG. 23 is an explanatory diagram for explaining a configuration of the information processing system 70 according to an eighth embodiment. The description of the parts common to the first embodiment will be omitted.

The information processing system 70 of the eighth embodiment includes a computer 90, a client 40, and a tag reader 39 that are connected via a network.

The computer 90 includes a control unit 51, a main storage device 52, an auxiliary storage device 53, a communication unit 54, a reading unit 57, and a bus. The computer 90 is an information device such as a general-purpose personal computer, a tablet, or a server computer.

A program 97 is recorded in a portable recording medium 96. The control unit 51 reads the program 97 via the reading unit 57 and stores the read program 97 in the auxiliary storage device 53. Further, the control unit 51 may read the program 97 stored in the semiconductor memory 98 such as a flash memory mounted in the computer 90. In addition, the control unit 51 may download the program 97 from the communication unit 54 and other server computers (not illustrated) connected via a network (not illustrated) and store the downloaded program 97 in the auxiliary storage device 53.

The program 97 is installed as a control program on the computer 90 and is loaded into and executed on the main storage device 52. As a result, the computer 90 functions as the server 50 described above.

The control unit 51 transmits the portion executed by the client 40 among the programs 97 to each client 40 via the network. The transmitted program is installed as the control program of the client 40 and is loaded into and executed on the main storage device 42. As a result, the client 40 and the computer 90 cooperate with each other to perform the function of the information processing system 70 described above.

The technical features (constituent requirements) described in each embodiment can be combined with each other, and a new technical feature can be formed by the combination.

The embodiments disclosed this time should be considered to be exemplary in all respects without being limited. The scope of the present invention is indicated by the scope of claims, not the above-mentioned meaning, and is intended to include all modifications within the meaning and scope equivalent to the claims.

REFERENCE SIGNS LIST

10 Endoscope
11 Soft portion
12 Bending section
13 Distal tip portion
131 Image sensor
132 Observation window
133 Illumination window
134 Through hole
136 Light emitting element
14 Insertion portion
15 Memory element
16 Stopper
18 Endoscope tag
19 Part tag
20 Operation unit
21 Bending knob
22 Channel entrance
23 Forceps plug
24 Connector unit
25 Universal code
26 Connector case
27 Scope connector
28 Light guide connector
29 Light guide
30 Endoscope system
31 Bed for endoscopic examination
32 Processor for endoscope
33 Display device
35 Keyboard
36 Housing rack
38 Collection container
39 Tag reader (reading device)
391 Reading unit
392 Transmitting unit
40 Client
41 Control unit
42 Main storage device
43 Auxiliary storage device
44 Communication unit
441 Receiving unit
442 Use information transmitting unit
49 Tag communication unit
50 Server
51 Control unit
52 Main storage device
53 Auxiliary storage device
54 Communication unit
551 Use information acquisition unit
552 Collection instruction output unit
553 Delivery instruction output unit
57 Reading unit
61 First endoscope DB
62 Second endoscope DB
63 Reusable part DB
65 Collection request DB
66 Slip DB
70 Information processing system
71 Housing container
96 Portable recording medium
97 Program
98 Semiconductor memory

The invention claimed is:
1. An information processing method, comprising:
acquiring use information indicating that a sterilized endoscope, in which a reusable part that is able to be used repeatedly and a non-reusable part that is able to be used only once are combined, is used;
outputting a collection instruction for collecting the endoscope corresponding to the acquired use information from a medical institution;
acquiring information on
a number of endoscopes for which inspection is scheduled by the medical institution, which is denoted as an inspection-schedule quantity,
a predetermined number of endoscopes for which no specific schedule for inspection by the medical institution is recorded, the predetermined number being denoted as an endoscope margin, and
a number of endoscopes recorded in an endoscope inventory of the medical institution, which is denoted as the inventory quantity;
outputting a delivery instruction for delivering a non-used replaceable endoscope to the medical institution in response to the collection instruction; and outputting a delivery instruction for instructing delivery of a non-used endoscope to the medical institution when equation (2) is not satisfied, wherein equation (2) comprises Inventory quantity>inspection schedule quantity+ endoscope margin.

2. The information processing method according to claim 1, further comprising:
acquiring a reusable part ID uniquely assigned to the reusable part removed from the collected endoscope;
assigning a unique endoscope ID to a new endoscope remanufactured using the reusable part; and
recording the endoscope ID and the reusable part ID in association with each other.

3. The information processing method according to claim 1, wherein
the reusable part includes
a light emitting element, and
an image sensor that captures an image of an object illuminated by light emitted from the light emitting element,
wherein the resuable part is a distal tip portion attached to an insertion portion of the endoscope.

4. The information processing method according to claim 1, wherein
the endoscope ID is recorded on the sterilized endoscope or a tag attached to a housing container that individually houses the sterilized endoscope, and
the use information is transmitted based on information read from the tag by a reading device arranged in the medical institution.

5. The information processing method according to claim 4, wherein
the tag is a wireless communication tag that is readable by short-range wireless communication.

6. The information processing method according to claim 1, further comprising:
collecting the used endoscopes from the medical institution and delivering the non-used replaceable endoscope to the medical institution, in a case where the use information on a predetermined number of the used endoscopes is acquired.

7. The information processing method according to claim 1, further comprising:
charging the medical institution based on the number of used endoscopes acquired by the use information acquiring operation or the number of delivered replaceable endoscopes.

8. An information processing device, comprising:
a use information acquisition unit that acquires use information indicating that a sterilized endoscope in which a reusable part that is able to be used repeatedly and a non-reusable part that is able to be used only once are combined is used in a medical institution;
a collection instruction output unit that outputs a collection instruction for collecting the endoscope from the medical institution when the use information acquisition unit acquires the use information;
an endoscope information acquiring unit that acquires information on a number of endoscopes for which inspection is scheduled by the medical institution, which is denoted as an inspection-schedule quantity,
a predetermined number of endoscopes for which no specific schedule for inspection by the medical institution is recorded, the predetermined number being denoted as an endoscope margin, and
a number of endoscopes recorded in an endoscope inventory of the medical institution, which is denoted as the inventory quantity;
a first delivery instruction output unit that outputs a delivery instruction for delivering a non-used replaceable endoscope to the medical institution in response to the collection instruction; and
a second delivery instruction output unit that outputs a delivery instruction for instructing delivery of a non-used endoscope to the medical institution when equation (2) is not satisfied, wherein equation (2) comprises Inventory quantity>inspection schedule quantity+ endoscope margin.

9. An information processing system, comprising:
a server;
a client connected to the server via a network; and
a reading device connected to the client, wherein
the reading device includes
a reading unit that reads an endoscope ID assigned to a single-use endoscope, and
a transmitting unit that transmits the endoscope ID read by the reading unit to the client,
the client includes
a receiving unit that receives the endoscope ID transmitted from the transmitting unit, and
a use information transmitting unit that transmits use information on the endoscope based on the endoscope ID received by the receiving unit, and
the server includes
a use information acquisition unit that acquires the use information transmitted from the use information transmitting unit,
a collection instruction output unit that outputs a collection instruction for collecting the endoscope from the medical institution when the use information acquisition unit acquires the use information;
an endoscope information acquiring unit that acquires information on a number of endoscopes for which inspection is scheduled by the medical institution, which is denoted as an inspection-schedule quantity,
a predetermined number of endoscopes for which no specific schedule for inspection by the medical institution is recorded, the predetermined number being denoted as an endoscope margin, and
a the number of endoscopes recorded in an endoscope inventory of the medical institution, which is denoted as the inventory quantity;
a first delivery instruction output unit that outputs a delivery instruction for delivering a non-used replaceable endoscope to the medical institution in response to the collection instruction; and
a second delivery instruction output unit that outputs a delivery instruction for instructing delivery of a non-used endoscope to the medical institution when equation (2) is not satisfied, wherein equation (2) comprises Inventory quantity>inspection schedule quantity+ endoscope margin.

\* \* \* \* \*